US007977095B2

(12) United States Patent
Bonyhadi et al.

(10) Patent No.: US 7,977,095 B2
(45) Date of Patent: Jul. 12, 2011

(54) GENERATION AND ISOLATION OF ANTIGEN-SPECIFIC T CELLS

(75) Inventors: Mark Bonyhadi, Issaquah, WA (US); Dale Kalamasz, Redmond, WA (US)

(73) Assignee: Life Technologies Corporation, Carlsbad, CA (US)

( * ) Notice: Subject to any disclaimer, the term of this patent is extended or adjusted under 35 U.S.C. 154(b) by 25 days.

(21) Appl. No.: 12/251,224

(22) Filed: Oct. 14, 2008

(65) Prior Publication Data

US 2009/0137017 A1  May 28, 2009

Related U.S. Application Data

(60) Continuation of application No. 11/674,304, filed on Feb. 13, 2007, now abandoned, which is a division of application No. 10/742,622, filed on Dec. 19, 2003, now abandoned.

(60) Provisional application No. 60/469,122, filed on May 8, 2003.

(51) Int. Cl.
*C12N 5/08* (2006.01)
*C12N 5/00* (2006.01)

(52) U.S. Cl. ...................... 435/372.3; 435/375; 435/405

(58) Field of Classification Search ........................ None
See application file for complete search history.

(56) References Cited

U.S. PATENT DOCUMENTS

| | | | |
|---|---|---|---|
| 5,057,423 A | 10/1991 | Hiserodt et al. | 435/240.23 |
| 5,081,029 A | 1/1992 | Zarling et al. | 435/172.3 |
| 5,190,878 A | 3/1993 | Wilhelm | 435/285 |
| 5,219,740 A | 6/1993 | Miller | |
| 5,443,983 A | 8/1995 | Ochoa et al. | 435/240.2 |
| 5,470,730 A | 11/1995 | Greenberg et al. | 435/172.3 |
| 5,547,963 A | 8/1996 | Poindron et al. | 514/317 |
| 5,595,881 A | 1/1997 | Kendrick et al. | 435/7.21 |
| 5,626,561 A | 5/1997 | Butler | |
| 5,635,697 A | 6/1997 | Shellhammer | |
| 5,672,505 A | 9/1997 | Jones et al. | 435/283.1 |
| 5,674,704 A | 10/1997 | Goodwin et al. | 435/69.1 |
| 5,735,279 A | 4/1998 | Klaveness et al. | 128/654 |
| 5,766,944 A | 6/1998 | Ruiz | 435/325 |
| 5,787,900 A | 8/1998 | Butler | |
| 5,804,442 A | 9/1998 | Romet-Lemonne et al. | 435/374 |
| 5,827,642 A | 10/1998 | Riddell et al. | 435/2 |
| 5,837,477 A | 11/1998 | Germain et al. | 435/7.24 |
| 5,843,069 A | 12/1998 | Butler | |
| 5,858,358 A * | 1/1999 | June et al. | 424/130.1 |
| 5,874,307 A | 2/1999 | Ohno et al. | 435/372.3 |
| 5,883,223 A | 3/1999 | Gray | 530/328 |
| 5,888,807 A | 3/1999 | Palsson et al. | 435/293.2 |
| 5,902,745 A | 5/1999 | Butler | |
| 5,913,998 A | 6/1999 | Butler | |
| 5,942,607 A | 8/1999 | Freeman et al. | 536/23.5 |
| 5,962,318 A | 10/1999 | Rooney et al. | 435/325 |
| 5,962,319 A | 10/1999 | Ogawa et al. | 435/325 |
| 5,972,721 A | 10/1999 | Bruno et al. | 436/526 |
| 5,980,889 A | 11/1999 | Butler | |
| 5,985,653 A | 11/1999 | Armstrong et al. | 435/303.1 |
| 6,008,188 A | 12/1999 | Oishi et al. | 514/2 |
| 6,010,902 A | 1/2000 | Ledbetter et al. | 435/328 |
| 6,074,635 A | 6/2000 | Abrignani | 424/85.1 |
| 6,096,532 A | 8/2000 | Armstrong et al. | 435/286.5 |
| 6,113,901 A | 9/2000 | Bluestone | 424/154.1 |
| 6,120,766 A | 9/2000 | Hale et al. | 424/130.1 |
| 6,129,916 A | 10/2000 | Chang | 424/179.1 |
| 6,143,297 A | 11/2000 | Bluestone | 424/184.1 |
| 6,184,043 B1 | 2/2001 | Fodstad et al. | 436/526 |
| 6,197,298 B1 | 3/2001 | Chang | 424/179.1 |
| 6,199,654 B1 | 3/2001 | Kojo | 180/443 |
| 6,207,453 B1 | 3/2001 | Maass | |
| 6,225,118 B1 | 5/2001 | Grant et al. | 435/347 |
| 6,274,378 B1 * | 8/2001 | Steinman et al. | 435/377 |
| 6,316,257 B1 | 11/2001 | Flyer et al. | 435/372.3 |
| 6,352,694 B1 | 3/2002 | June et al. | 424/93.71 |
| 6,355,779 B1 | 3/2002 | Goodwin et al. | 530/388.23 |
| 6,534,055 B1 | 3/2003 | June et al. | 424/93.71 |
| 6,797,514 B2 | 9/2004 | Berenson | 435/372 |
| 6,867,041 B2 * | 3/2005 | Berenson et al. | 435/377 |
| 6,887,466 B2 | 5/2005 | June | 424/93.7 |
| 6,905,680 B2 | 6/2005 | June | |
| 7,638,325 B2 | 12/2009 | June | 435/325 |
| 2001/0031253 A1 | 10/2001 | Gruenberg | 424/93.1 |
| 2002/0076407 A1 | 6/2002 | June et al. | 424/143.1 |
| 2002/0090362 A1 | 7/2002 | Stauss | 424/93.21 |
| 2002/0115214 A1 | 8/2002 | June et al. | 435/372.3 |
| 2002/0155604 A1 | 10/2002 | Ledbetter et al. | 435/372.3 |
| 2002/0182730 A1 | 12/2002 | Gruenberg | 435/375 |
| 2003/0039650 A1 | 2/2003 | Gruenberg | 424/144.1 |

(Continued)

FOREIGN PATENT DOCUMENTS

EP            440 373 A1      8/1991

(Continued)

OTHER PUBLICATIONS

Campbell et al., J of Immunol. 2001, v.167, pp. 553-561.*
Altman et al., "Phenotypic analysis of antigen-specific T lymphocytes," *Science* 274(5284):94-96, 1996.
Arenz et al., "Antigen-independent in vitro expansion of T cells does not affect the T cell receptor Vβ repertoire," *J. Mol. Med.* 75:678-686, 1997.
Azuma et al., "B70 antigen is a second ligand for CTLA-4 and CD28," *Nature* 366(6450):76-79, Nov. 4, 1993.
Baroja et al., "The Anti-T Cell Monoclonal Antibody 9.3 (Anti-CD28) Provides a Helper Signal and Bypasses the Need for Accessory Cells in T Cell Activation with Immobilized Anti-CD3 and Mitogens," *Cellular Immunology* 120:205-217, 1989.
Berenson, "Engraftment After Infusion of CD34+ Marrow Cells in Patients With Breast Cancer or Neuroblastoma," *Blood* 77(8):1717-1722, Apr. 15, 1991.

(Continued)

*Primary Examiner* — Michail Belyavskyi
(74) *Attorney, Agent, or Firm* — Seed IP Law Group PLLC

(57) ABSTRACT

The present invention relates generally to methods for generating, expanding, and isolating antigen-specific T cells. Compositions of antigen-specific T cells activated and expanded by the methods herein are further provided.

14 Claims, 7 Drawing Sheets

U.S. PATENT DOCUMENTS

| | | | |
|---|---|---|---|
| 2003/0099643 A1 | 5/2003 | June et al. | 424/144.1 |
| 2003/0119185 A1 | 6/2003 | Berenson | 435/372 |
| 2003/0124122 A1 | 7/2003 | Berenson et al. | 424/144.1 |
| 2003/0134341 A1 | 7/2003 | Gruenberg | 435/7.21 |
| 2003/0134415 A1 | 7/2003 | Gruenberg | 435/372 |
| 2003/0170238 A1 | 9/2003 | Gruenberg et al. | 424/144.1 |
| 2003/0175242 A1 | 9/2003 | Gruenberg | 424/93.2 |
| 2003/0175272 A1 | 9/2003 | Gruenberg | 424/144.1 |
| 2003/0194395 A1 | 10/2003 | Gruenberg et al. | 424/93.7 |
| 2003/0224520 A1 | 12/2003 | June et al. | 435/455 |
| 2003/0235908 A1 | 12/2003 | Berenson et al. | 435/372 |

FOREIGN PATENT DOCUMENTS

| | | |
|---|---|---|
| EP | 440 373 B1 | 4/1997 |
| EP | 633 930 B1 | 4/2000 |
| EP | 690125 B1 | 4/2003 |
| WO | WO 94/29436 | 12/1994 |
| WO | WO 97/01304 | 1/1997 |
| WO | WO 97/05233 | 2/1997 |
| WO | WO 97/05239 | 2/1997 |
| WO | WO 97/34618 | 9/1997 |
| WO | WO 9722349 * | 9/1997 |
| WO | WO 97/44667 | 11/1997 |
| WO | WO 99/24045 | 5/1999 |
| WO | WO 00/02520 | 1/2000 |
| WO | WO 01/62895 | 8/2001 |
| WO | WO 01/85920 | 11/2001 |
| WO | WO 02/087627 | 11/2002 |
| WO | WO 02/098361 | 12/2002 |
| WO | WO 03/000339 | 1/2003 |
| WO | WO 03/024312 | 3/2003 |
| WO | WO 03/024989 | 3/2003 |
| WO | WO 03/025158 | 3/2003 |
| WO | WO 03/034820 | 5/2003 |
| WO | WO 03/043643 | 5/2003 |
| WO | WO 03/077658 | 9/2003 |

OTHER PUBLICATIONS

Bergstresser et al., "T Cell-Mediated Terminal Maturation of Dendritic Cells," in *Dendritic Cell in Fundamental and Clinical Immunology*, Ricciardi-Castagnoli (Ed.), Plenum Press, New York, 1997, pp. 65-69.

Bishop et al., "High-Dose Therapy and Peripheral Blood Progenitor Cell Transplantation: Effects of Recombinant Human Granulocyte-Macrophage Colony-Stimulating Factor on the Autograft," *Blood* 83(2):610-616, Jan. 15, 1994.

Bonini et al., "HSV-TK Gene Transfer into Donor Lymphocytes for Control of Allogeneic Graft-Versus-Leukemia," *Science* 276:1719-1724, Jun. 13, 1997.

Bonyhadi et al., "Xcellerate: an Autologous T Cell Immunotherapy Approach for Treating B-Cell Lymphocytic Leukemia (B-CLL)," *Blood* 96(11):837a, Nov. 16, 2000.

Bonyhadi et al., "Autologous T Cell Therapy for B-CLL," *Blood* 100(11), Abstract No. 774, Nov. 6, 2002.

Bretscher, "The two-signal model of lymphocyte activation twenty-one years later," *Immunology Today* 13(2):74-76, 1992.

Broder, "The Suppressor-Cell Network in Cancer," *The New England Journal of Medicine* 299(23):1281-1284, Dec. 7, 1978.

Carlens et al., "Ex vivo T lymphocyte expansion for retroviral transduction: Influence of serum-free media on variations in cell expansion rates and lymphocyte subset distribution," *Experimental Hematology* 28:1137-1146, 2000.

Cohen et al., "T-Cell Adoptive Therapy of Tumors: Mechanisms of Improved Therapeutic Performance," *Critical Reviews in Immunology* 21:215-248, 2001.

Creson et al., "The Mode and Duration of Anti-CD28 Costimulation Determine Resistance to Infection by Macrophage-Tropic Strains of Human Immunodeficiency Virus Type 1 in Vitro," *Journal Of Virology* 73(11):9337-9347, Nov. 1999.

Dal Porto et al., "A soluble divalent class I major histocompatibility complex molecule inhibits alloreactive T cells at nanomolar concentrations," *Proc. Natl. Acad. Sci. USA* 90:6671-6675, Jul. 1993.

Dietrich et al., "TCR analysis reveals significant repertoire selection during in vitro lymphocyte culture," *International Immunology* 9(8):1073-1083, 1997.

Freedman et al., "B7, A B Cell-Restricted Antigen that Identifies Preactivated B Cells," *J. Immunol.* 137(10):3260-3267, Nov. 15, 1987.

Freeman et al., "B7, a new member of the Ig superfamily with unique expression on activated and neoplastic B cells," *J. Immunol.* 143(8):2714-2722, Oct. 15, 1989.

Freeman et al., "Cloning of B7-2: a CTLA-4 counter-receptor that costimulates human T cell proliferation," *Science* 262(5135):909-911, Nov. 5, 1993.

Freeman et al., "Murine B7-2, an alternative CTLA4 counter-receptor that costimulates T cell proliferation and interleukin 2 production," *J. Exp. Med.* 178(6):2185-2192, Dec. 1993.

Freeman et al., "Structure, expression, and T cell costimulatory activity of the murine homologue of the human B lymphocyte activation antigen B7," *J. Exp. Med.* 174(3):625-631, Sep. 1991.

Frohlich et al. "Ex Vivo Activation and Expansion of T Cells from the Peripheral Blood of Multiple Myeloma Patients Using the Xcellerate™ Process," *Blood* 100(11), Abstract No. 5259, Nov. 16, 2002.

Gailit et al., "Wound repair in the context of extracellular matrix," *Curr. Opin. Cell. Biol.* 6(5):717-725, Oct. 1994.

Garland et al., "The use of Teflon cell culture bags to expand functionally active CD8+ cytotoxic T lymphocytes," *Journal of Immunological Methods* 227:53-63, 1999.

Groh et al., "Stimulation of T cell autoreactivity by anomalous expression of NKG2D and its MIC ligands in rheumatoid arthritis," *Proceedings of the National Academy of Sciences* 100(16):9452-9457, Aug. 5, 2003.

Grosmaire et al., "Ligation of CD2 Amplifies Anti-CD3 X Anti-CD28-Mediated Ex Vivo Activation and Expansion of T Cells," *Blood* 96(11 part 2):40b, Abstract No. 3834, Nov. 16, 2000.

Haanen et al., "Selective Expansion of Cross-reactive CD8+ Memory T Cells by Viral Variants," *J. Exp. Med.* 190(9):1319-1328, Nov. 1, 1999.

Hami et al., "Xcellerate™: A Platform Process for the GMP Manufacture of Activated T Cells for the Treatment of Patients with Cancer and Immune Dysfunction," in *Proceedings of the 42nd Annual Meeting of the American Society of Hematology*, San Francisco, Dec. 1-5, 2000, vol. 96, No. 11, part 1, abstract # 3630.

Hancock et al., "Keratinocyte growth regulation by the products of immune cells," *J. Exp. Med.* 168:1395-1402, Oct. 1988.

Hou et al., "Naïve (CD45RA+) vs Memory (CD45RO+) Status of Human CD4 Cells Greatly Influence Th1/Th2 Polarization Potential," *Blood* 100(11), Abstract No. 944, Nov. 16, 2002.

Husebekk et al., "Selection and expansion of T cells from untreated patients with CLL: source of cells for immune reconstitution," *Cytotherapy* 2(3):187-193, 2000.

Iezzi et al., "The Duration of Antigenic Stimulation Determines the Fate of Naive and Effector T Cells," *Immunity* 8:89-95, Jan. 1998.

Imura et al., "The human OX40/gp34 system directly mediates adhesion of activated T cells to vascular endothelial cells," *J. Exp. Med* 183:2185-2195, May 1996.

Iruela-Arispe et al., "Thrombospondin exerts an antiangiogenic effect on cord formation by endothelial cells in vitro," *Proc. Natl. Acad. Sci. USA*. 88(11):5026-5030, Jun. 1991.

Izumi et al., "Transforming growth factor $\beta_1$ stimulates type II collagen expression in cultured periosteum-derived cells," *Journal of Bone and Mineral Research* 7(1):115-121, Jan. 1992.

Jingushi et al.,"Acidic Fibroblast Growth Factor (aFGF) Injection Stimulates Cartilage Enlargement and Inhibits Cartilage Gene Expression in Rat Fracture Healing," *Journal of Orthopaedic Research* 8(3):364-371, May 1990.

Joyce et al., "Transforming growth factor-beta and the initiation of chondrogenesis and osteogenesis in the rat femur," *J. Cell. Biol.* 110(6):2195-207, Jun. 1990.

June et al., "The B7 and CD28 receptor families," *Immunology Today* 15(7):321-331, 1994.

June et al., "Methods for Selectively Stimulating Proliferation of T-Cells," U.S. Appl. No. 08/253,964, filed Jun. 3, 1994.

Kalamasz et al., "Storage Shipment of Freshly Harvested or Cryopreserved Xcellerate™ Activated T Cells for Clinical Applications," in *Proceedings of the 42nd Annual Meeting of the American Society of Hematology*, San Francisco, Dec. 1-5, 2000, vol. 96, No. 11 part 2, abstract # 5113.

Kato et al., "Gene Transfer of CD40-Ligand Induces Autologous Immune Recognition of Chronic Lymphocytic Leukemia B Cells," *J. Clin. Invest.* 101(5):1133-1141, Mar. 1998.

Kern et al., "Cancer Cachexia,"*Journal of Parenteral and Enteral Nutrition* 12(3):286-298, 1998.

Krawczyk et al., "Cbl-b Is a Negative Regulator of Receptor Clustering and Raft Aggregation in T Cells," *Immunity* 13:463-473, Oct. 2000.

Landevirta et al., "Elevated levels of circulating cachectin/tumor necrosis factor in patients with acquired immunodeficiency syndrome," *Am. J. Med.* 85(3):289-291, Sep. 1988.

Lanzavecchia, "The Role of Dendritic Cells in the Generation of Effector and Memory T Cell Responses," from *The Midwinter Conference of Immunologists*, Jan. 22-25, 2000, available at www.midwconfimmnunol.org/Midwinter00/sessions/lanzavecchia.html.

Larsen et al., "The ratio of anti-CD3 and anti-CD28 stimulation determines proliferation and IL-2R expression in T cells," *Tissue Antigens* 55(Suppl. 1):No. T11, p. 109, 2000.

Larsson et al., "Productive Cytomegalovirus (CMV) Infection Exclusively in CD13-Positive Peripheral Blood Mononuclear Cells from CMV-Infected Individuals," *Transplantation* 65(3):411-415, Feb. 15, 1998.

Levings et al., "Human $CD25^+$ $CD4^+$ T regulatory cells suppress naïve and memory T cell proliferation and can be expanded in vitro without loss of function," *J. Exp. Med.* 193(11):1295-1302, Jun. 2001.

Li et al., "Expanded Tumor-reactive $CD4^+$ T-Cell Responses to Human Cancers Induced by Secondary Anti-CD3/Anti-CD28 Activation," *Clinical Cancer Research* 5:461-469, Feb. 1999.

Li et al., "Immunological Effects of BCG as an Adjuvant in Autologous Tumor Vaccines," *Clinical Immunology* 94(1):64-72, Jan. 2000.

Liebowitz et al., "Costimulatory approaches to adoptive immunotherapy," *Current Opinion in Oncology* 10:533-541, 1998.

Lin et al., "Stability and Diveristy of T Cell Receptor Repertoire Usage during Lymphocytic Choriomenigitis Virus Infection of Mice," *Journal of Experimental Medicine* 188(11):1993-2005, Dec. 7, 1998.

Liu et al., "Calceneurin is a common target of cyclophilin-cyclosporin A and FKBP-FK506 complexes," *Cell* 66(4):807-815, Aug. 23, 1991.

Long et al., "Modulating T Cell Signals Using Xcyte™ Dynabeads® Leads to Selective Expansion of Antigen-Specific T Cells," *Blood* 102(11):55b, Abstract No. 3922, Nov. 16, 2003.

Lopez et al., "CD58/LFA-3 and IL-12 provided by activated monocytes are critical in the in vitro expansion of $CD56^+$ T cells," *Cancer Immunol. Immunother.* 49:629-640, 2001.

Marijt et al., "Specific T Cell Therapy in Leukemia," *Journal of Hematotherapy & Stem Cell Research* 10:493-500, 2001.

Meuer et al., "An alternative pathway of T-cell activation: a functional role for the 50 kd T11 sheep erythrocyte receptor protein," *Cell* 36(4):897-906, Apr. 1984.

Moebius et al., "T cell receptor gene rearrangements of T lymphocytes infiltrating the liver in chronic active hepatitis B and primary biliary cirrhosis (PBC): oligoclonality of PBC-derived T cell clones," *Eur. J. Immunol.* 20:889-896, 1990.

Nijhuis et al., "Stochastic processes strongly influence HIV-1 evolution during suboptimal protease-inhibitor therapy," *Proc. Natl. Acad. Sci. USA* 95:14441-14446, Nov. 1998.

Patel et al., "Optimization of conditions for specific binding of antibody-coated beads to cells," *Journal of Immunological Methods* 184:71-80, 1995.

Polanski et al., "Xcellerate: A Closed, Scalable Process for the GMP Manufacture of Stable Activated T Cells," in *Proceedings of the 15$^{th}$ Annual Scientific Meeting of the Society for Biological Therapy*, Seattle, Oct. 26-29, 2000, and *Journal of Immunotherapy* (23)5:599, Sep. 2000.

Ranheim et al., "Activated T Cells Induce Expression of B7/BB1 on Normal or Leukemic B Cells through a CD40-dependent Signal," *J. Exp. Med.* 177:925-935, Apr. 1993.

Ria et al., "Molecular Characterization of the T Cell Repertoire Using Immuno-scope Analysis and its Possible Implementation in Clinical Practice," *Current Molecular Medicine* 1:297-304, 2001.

Riddell et al., "T-Cell Therapy of Leukemia," *Cancer Control* 9(2):114-122, Mar./Apr. 2002.

Riddell et al., "The use of anti-CD3 and anti-CD28 monoclonal antibodies to clone and expand human antigen-specific T cells," *Journal of Immunological Methods* 128:189-201, 1990.

Sage et al., "Collagen synthesis by bovine aortic endothelial cells in culture," *Biochemistry* 18(24):5433-5442, Nov. 27, 1979.

Sakaguchi et al., "Immunologic tolerance maintained by CD25+ CD4+ regulatory T cells: their common role in controlling autoimmunity, tumor immunity, and transplantation tolerance," *Immunol. Rev.* 182:18-32, Aug. 2001.

Salomon et al., "B7/CD28 costimulation is essential for the homeostasis of the CD4+CD25+ immunoregulatory T cells that control autoimmune diabetes," *Immunity* 12(4):431-440, Apr. 2000.

Scanlan et al., "Molecular cloning of fibroblast activation protein, α, a member of the serine protease family selectively expressed in stromal fibroblasts of epithelial cancers," *Proc. Natl. Acad. Sci. USA* 91:5657-5661, Jun. 1994.

Shevach, "Regulatory T cells in autoimmunity," *Annu. Rev. Immunol.* 18:423-449, 2000.

Shimizu et al., "Large-Scale ex Vivo Expansion of Primary T Lymphocytes in Late-Stage AIDS Patients," *AIDS Research and Human Retroviruses* 16(6):611-612, 2000.

Staiano-Coico et al., "Human keratinocyte culture. Identification and staging of epidermal cell subpopulations," *J. Clin. Invest.* 77(2):396-404, Feb. 1986.

Stephens et al., "Human $CD4^+$ $CD25^+$ thymocytes and peripheral T cells have immune suppressive activity in vitro," *Eur. J. Immunol.* 31(4):1247-1254, Apr. 2001.

Stohl et al., "Polyclonal in Vitro T Cell Proliferation and T Cell-Dependent B Cell Differentiation Supported by Activated Autologous B Cells," *Clinical Immunology and Immunopathology* 72(1):44-52, Jul. 1994.

Tao et al., "Conservation of Epstein-Barr Virus Cytotoxic T-Cell Epitopes in Posttransplant Lymphomas. Implications for Immune Therapy," *American Journal of Pathology* 160(5):1839-1845, May 2002.

ten Berge et al., "Selective Expansion of a Peripheral Blood $CD8^+$ Memory T Cell Subset Expressing Both Granzyme B and $_L$-Selectin During Primary Viral Infection in Renal Allograft Recipients," *Transplantation Proceedings* 30:3975-3977, 1998.

Tolsma et al., "Peptides derived from two separate domains of the matrix protein thrombospondin-1 have anti-angiogenic activity," *J. Cell. Biol.* 122(2):497-511, Jul. 1993.

Vathsala et al., "Inhibition of Apoptosis in Anti-CD3-Treated Peripheral Blood Lymphocytes by Immunosuppressive Drugs," *Transplantation Proceedings* 32:1992-1994, 2000.

Vogel et al., "Modulation of endothelial cell proliferation, adhesion, and motility by recombinant heparin-binding domain and synthetic peptides from the type 1 repeats of thrombospondin," *J. Cell. Biochem.* 53(1):74-84, Sep. 1993.

Woo et al., "Cutting Edge: Regulatory T Cell from Lung Cancer Patients Directly Inhibit Autologous T Cell Proliferation," *The Journal of Immunology* 168:4272-4276, 2002.

Yamada et al., "Clonal T-cell proliferation causing pure red cell aplasia in chronic B-cell lymphocytic leukaemia: successful treatment with cyclosporine following in vitro abrogation of erythroid colony-suppressing activity," *British Journal of Haematology* 101:335-337, 1998.

Yang et al., "A common pathway for T lymphocyte activation involving both the CD3-Ti complex and CD2 sheep erythrocyte receptor determinants," *J. Immunol.* 137(4):1097-1100, Aug. 15, 1986.

Zou et al., "Tumor-Bearing Mice Exhibit a Progressive Increase in Tumor Antigen-Presenting Cell Function and A Reciprocal Decrease in Tumor Antigen-Responsive $CD4^+$ T Cell Activity," *The Journal of Immunology* 148(2):648-655, Jan. 15, 1992.

Asseman et al., "About CD4+ CD25+ regulatory cells," *Autoimmun. Rev.* 1(4):190-197, 2002.

Bartlett et al., "A Phase II Study of Xcellerated T Cells™ in Patients with Relapsed or Refractory Indolent Non-Hodgkin's Lymphoma (NHL)," *Blood (ASH Annual Meeting Abstracts)* 104:Abstract 4640, 2004.

Bauer et al., "Large Scale Ex Vivo GMP Expanded, Activated Human T Cells Consistently Induce Lethal GvHD in a Mouse Xenotransplant Model—A New Way to Study Treatments for Acute GvHD," *Blood (Abstracts of the American Society of Hematology 47th annual meeting*, Dec. 10-13, 2005, Atlanta, Georgia, USA) 106:Abstract 5242, 2005.

Berenson et al., "Xcellerate™ Therapy: A Novel Therapeutic Strategy for the Treatment of Autoimmune Diseases," *Blood (Abstracts of the American Society of Hematology 45th Annual Meeting*. Dec. 6-9, 2003. San Diego, California, USA) 102:Abstract 839, 2003.

Berenson et al., "A Randomized Phase II Study of Xcellerated T Cells™ with or without Prior Fludarabine Therapy in Patients with Relapsed or Refractory Multiple Myeloma," *Blood (Abstracts of the American Society of Hematology 46th Annual Meeting*. Dec. 4-7, 2004, San Diego, California, USA) 104:Abstract 2410, 2004.

Berenson et al., "Combined Cytoreduction and Infusion of Anti-CD3/Anti-CD28 Bead-Activated T Cells Prevent Diabetes in NOD Mice," *Blood (Abstracts of the American Society of Hematology 47th annual meeting*, Dec. 10-13, 2005, Atlanta, Georgia, USA) 106:Abstract 3036, 2005.

Berenson et al., "Anti-CD3/Anti-CD28 Bead-Activated T Cells Facilitate Engraftment of Murine Histoincompatible Allogeneic Transplants after Low-Dose Radiation," *Blood (Abstracts of the American Society of Hematology 47th annual meeting*, Dec. 10-13, 2005, Atlanta, Georgia, USA) 106:Abstract 5221, 2005.

Berger et al., "CD28 costimulation and immunoaffinity-based selection efficiently generate primary gene-modified T cells for adoptive immunotherapy," *Blood 101*(2):476-484, 2003.

Bierer et al., "Cyclosporin A and FK506: molecular mechanisms of immunosuppression and probes for transplantation biology," *Curr. Opin. Immun. 5*:763-773, 1993.

Bondanza et al., "Suicide Gene Therapy of Graft-Versus-Host Disease Induced by Central Memory Human T Lymphocytes," *Blood (Abstracts of the American Society of Hematology 47th annual meeting*, Dec. 10-13, 2005, Atlanta, Georgia, USA) 106:Abstract 3096, 2005.

Bondanza et al., "Suicide gene therapy of graft-versus-host disease induced by central memory human T lymphocytes," *Blood 107*:1828-1836, 2006.

Bonyhadi et al., "In vitro engagement of CD3 and CD28 corrects T cell defects in chronic lymphocytic leukemia," *J. Immunol*, 174:2366-2375, 2005.

Bonyhadi et al., "Expansion of Antigen-Specific CTL Using CD3/CD28 Paramagnetic Microbeads(Xcellate TM Beads), for Adoptive Cellular Therapy of Melanoma," *Blood*, W. B. Saunders Company 98(11, 16):32B-33B, 2001.

Boris-Lawrie et al., "Recent advances in retrovirus vector technology," *Curr. Opin. Genet. Develop. 3*:102-109:1993.

Borrello et al., "A phase I/II study of Xcellerated T Cells after autologous peripheral blood stem cell transplantation in patients with multiple myeloma," *J. Clin. Oncol. (ASCO Annual Meeting Proceedings)* 22:Abstract 2540, 2004.

Burns et al., "Vesicular Stomatitis Virus G. Glycoprotein Pseudotyped Retroviral Vectors: Concentration to Very High Titer and Efficient Gene Transfer into Mammalian and Nonmammalian Cells", *PNAS USA 90*:8033-8037, 1993.

Carroll et al., "Differential regulation of HIV-1 fusion cofactor expression by CD28 costimulation of CD4+ T cells," *Science 276*:273-276, 1997.

Castro et al., "A Phase I/II Trial of Xcellerated T Cells™ in Patients with Chronic Lymphocytic Leukemia," *Blood (Abstracts of the American Society of Hematology 46th Annual Meeting*. Dec. 4-7, 2004, San Diego, California, USA) 104:Abstract 2508, 2004.

Coito et al., "Retrovirus-mediated gene transfer in human primary T lymphocytes induces an activation-and transduction/selection-dependent TCR-B variable chain repertoire skewing of gene-modified cells," *Stem Cells and Development 13*:71-81, 2004.

Curotto de Lafaille et al., "CD4(+) regulatory T cells in autoimmunity and allergy," *Curr. Opin. Immunol*, 14(6):771-778, 2002.

Dang et al., "Tumor antigen—specific T-cell expansion is greatly facilitated by in vivo priming," *Clin. Cancer Res. 13*:1883-1891, 2007.

Deeks et al., "A phase II randomized study of HIV-specific T-cell gene therapy in subjects with undetectable plasma viremia on combination antiretroviral therapy," *Molecular Therapy 5*:788-797, 2002.

During et al., "Gastric Secretion During a Medical Interview," *Ann. Neurol. 25*:351, 1989.

Earle et al., "In vitro expanded human CD4+CD25+ regulatory T cells suppress effector T cell proliferation," *Clin. Immunol. 115*:3-9, 2005.

Ferrand et al., "Retrovirus-mediated gene transfer in primary T lymphocytes: influence of the transduction/selection process and of ex vivo expansion on the T cell receptor beta chain hypo-variable region repertoire," *Human Gene Therapy 11*:1151-1164, 2000.

Fowler et al. "Phase I clinical trial of donor T-helper type-2 cells after immunoablative, reduced intensity allogeneic PBSC transplant," *Cytotherapy 4*:429-430, 2002.

Garlie et al., "T cells coactivated with immobilized anti-CD3 and anti-CD28 as potential immunotherapy for cancer," *J. Immunother.* 22:336-345, 1999.

Glode et al., "A phase I/II trial of CD3/CD28 activated T cells (Xcellerated T Cells) in patients with hormone refractory prostate cancer," *Journal of Clinical Oncology*, 2004 ASCO Annual Meeting Proceedings (Post-Meeting Edition)vol. 22, No. 14S (Jul. 15 Supplement):2549, 2004.

Godfrey et al., "In vitro-expanded human CD4(+)CD25(+) T-regulatory cells can markedly inhibit allogeneic dendritic cell-stimulated MLR cultures," *Blood 104*:453-461, 2004.

Godfrey et al., "Cord blood CD4(+)CD25(+)-derived T regulatory cell lines express FoxP3 protein and manifest potent suppressor function," *Blood 105*:750-758, 2005.

Green et al., "A Four-Color Flow Cytometry-Based Assay for Detection of Residual Leukemic B Cells in Xcellerated T Cells™ for Infusion into CLL Patients," *Blood (Abstracts of the American Society of Hematology 45th Annual Meeting*. Dec. 6-9, 2003. San Diego, California, USA) 102:Abstract 5426, 2003.

Gribben et al., "A Phase II Study of Xcellerated T Cells™ in Patients with Relapsed or Refractory Indolent Non-Hodgkin's Lymphoma (NHL)," *Journal of Clinical Oncology*, 2005 ASCO Annual Meeting Proceedings. vol. 23, No. 16S, Part I of II (Jun. 1 Supplement): 2510, 2005.

Hami et al., "Comparability of Xcellerated T Cells™ Manufactured Using a Static Culture Process and a Bioreactor Process for the Treatment of Patients with Multiple Myeloma," *Blood (Abstracts of the American Society of Hematology 45th Annual Meeting*. Dec. 6-9, 2003. San Diego, California, USA) 102:Abstract 3592, 2003.

Hami et al., "Reproducibility and Robustness of the Xcellerate III Process for the GMP Manufacture of Xcellerated T Cells™ for Infusion into CLL Patients," *Blood (Abstracts of the American Society of Hematology 46th Annual Meeting*. Dec. 4-7, 2004, San Diego, California, USA) 104:Abstract 4995, 2004.

Hami et al., "GMP production and testing of Xcellerated T Cells for the treatment of patients with CLL," *Cytotherapy 6*(6):554-62, 2004.

Henderson et al., "Comparison of the effects of FK-506, cyclosporin A and rapamycin on IL-2 production," *Immun. 73*:316-321, 1991.

Howard et al., "Intracerebral Drug Delivery in Rats with Lesion-induced Memory Deficits," *J. Neurosurg. 71*:105, 1989.

Humeau et al., "Efficient lentiviral vector-mediated control of HIV-1 replication in CD4 lymphocytes from diverse HIV+ infected patients grouped according to CD4 count and viral load," *Molecular Therapy 9*:902-913, 2004.

Janetzki et al., "AN. Insect cells as HLA-restricted antigen-presenting cells for the IFN-gamma elispot assay," *J Immunol Methods.* 234(1-2):1-12, 2000.

Kalamasz et al., "Optimization of human T-cell expansion ex vivo using magnetic beads conjugated with anti-CD3 and anti-CD28 antibodies," *J. Immunother. 27*:405-418, 2004.

Karakhanova et al., "Highly efficient expansion of human CD4+CD25+ regulatory T cells for cellular immunotherapy in patients with graft-versus-host disease," *J. Immunother. 29*:336-349, 2006.

Keever-Taylor et al., "Rapamycin enriches for CD4+ CD25+ CD27+ Foxp3+ regulatory T cells in ex vivo-expanded CD25-enriched products from healthy donors and patients with multiple sclerosis," *Cytother.* 9:144-157, 2007.

Kipps et al., "A Phase I/II Trial of Xcellerated T Cells™ in Patients with Chronic Lymphocytic Leukemia (CLL)," *Blood (Abstracts of the American Society of Hematology 45th Annual Meeting.* Dec. 6-9, 2003. San Diego, California, USA) 102:Abstract 370, 2003.

Kipps et al., "A Phase I/II Study of Xcellerated T Cells™ in Patients with Chronic Lymphocytic Leukemia," *Journal of Clinical Oncology*, 2005 ASCO Annual Meeting Proceedings. vol. 23, No. 16S, Part I of II (Jun. 1 Supplement):2511, 2005.

Langer et al., "Medical Applications of Controlled Release," *CRC Pres.* 2:115-138, 1984.

Langer et al., "New methods of drug delivery," *Science* 249:1527-1533, 1990.

Laport et al., "Adoptive transfer of costimulated T cells induces lymphocytosis in patients with relapsed/refractory non-Hodgkin lymphoma following CD34+-selected hematopoietic cell transplantation," *Blood* 102:2004-2013, 2003.

Levine et al., "Large-scale production of CD4+ T cells from HIV-1-infected donors after CD3/CD28 costimulation," *J. Hematother.* 7:437-448, 1998.

Levine et al., "Effects of CD28 costimulation on long-term proliferation of CD4+ T cells in the absence of exogenous feeder cells," *J. Immunol.* 159:5921-5930, 1997.

Levine et al., "Adoptive transfer of costimulated CD4+ T cells induces expansion of peripheral T cells and decreased CCR5 expression in HIV infection," *Nat. Med.* 8:47-53, 2002.

Levine et al., "Antiviral effect and ex vivo CD4+ T cell proliferation in HIV-positive patients as a result of CD28 costimulation," *Science* 272:1939-1943, 1996.

Levy et al., "Inhibition of calcification of bioprosthetic heart valves by local controlled-release diphosphonate," *Science* 228:190, 1985.

Li et al., "CD4+CD25+ regulatory T-cell lines from human cord blood have functional and molecular properties of T-cell anergy," *Blood* 106:3068-3073, 2005.

Long et al., "Restoring a Normal T Cell Receptor Repertoire Using the Xcellerate™ Technology: A Potential Therapeutic Strategy for Patients with Hematological Disorders and Autoimmune Diseases," *Blood (Abstracts of the American Society of Hematology 46th Annual Meeting.* Dec. 4-7, 2004, San Diego, California, USA) 104:Abstract 3853, 2004.

Long et al., "Activated and Expanded T Cells for Potential Therapy of Patients with Autoimmune Diseases," *Blood (Abstracts of the American Society of Hematology 46th Annual Meeting.* Dec. 4-7, 2004, San Diego, California, USA) 104:Abstract 3854, 2004.

Lum et al., "Immune modulation in cancer patients after adoptive transfer of anti-CD3/anti-CD28-costimulated T cells-phase I clinical trial," *J. Immunother.* 24:408-419, 2001.

Miller, "Retrovirus Packaging Cells," *Human Gene Therapy* 1:5-14, 1990.

Miller et al., "Improved Retroviral Vectors for Gene Transfer and Expression," *BioTechniques* 7:980-990, 1989.

Mitsuyasu et al., Prolonged survival and tissue trafficking following adoptive transfer of CD4zeta gene-modified autologous CD4(+) and CD8(+) T cells in human immunodeficiency virus-infected subjects *Blood* 96:785-793, 2000.

Nervi et al., "In Vivo Suicide Gene Therapy of Human T Lymphocytes to Prevent Graft Versus Host Disease in a Murine Xenograft Model," *Blood (Abstracts of the American Society of Hematology 46th Annual Meeting.* Dec. 4-7, 2004, San Diego, California, USA) 104:Abstract 4979, 2004.

Nervi et al., "Naive and Ex Vivo Activated Human T Cells Generate Consistent Engraftment and Lethal Graft-Versus-Host Disease (GvHD) in NOD SCID β 2M Null Mice: A New Xenogeneic Model for GvHD," *Blood (Abstracts of the American Society of Hematology 47th annual meeting*, Dec. 10-13, 2005, Atlanta, Georgia, USA) 106:Abstract 3106, 2005.

Noonan et al., "Activated marrow-infiltrating lymphocytes effectively target plasma cells and their clonogenic precursors," *Cancer Res.* 65:2026-2034, 2005.

Noonan et al., "CD4+CD25+ Marrow Infiltrating Lymphocytes in Myeloma Patients Display an Activated Phenotype and Lack Suppressive Function," *Blood (ASH Annual Meeting Abstracts)*, 108:Abstract 1741, 2006.

Onlamoon et al., "Optimization of in vitro expansion of macaque CD4 T cells using anti-CD3 and co-stimulation for autotransfusion therapy," *J. Med. Primatol.* 35:178-193, 2006.

Parmar et al., "Ex vivo expanded umbilical cord blood T cells maintain naive phenotype and TCR diversity," *Cytother.* 8:149-157, 2006.

Porter et al., "A phase 1 trial of donor lymphocyte infusions expanded and activated ex vivo via CD3/CD28 costimulation," *Blood* 107:1325-1331, 2006.

Rapoport et al., "Molecular remission of CML after autotransplantation followed by adoptive transfer of costimulated autologous T cells," *Bone Marrow Transplantation* 33:53-60, 2004.

Rapoport et al., "Restoration of immunity in lymphopenic individuals with cancer by vaccination and adoptive T-cell transfer," *Nat. Med.* 11:1230-1237, 2005.

Rettig et al., "Comparison of the Proliferative Kinetics, GVHD Potential and GCV Sensitivity of Naive and Transduced and Selected Murine T Cells after Allogeneic BMT," *Blood (Abstracts of the American Society of Hematology 47th annual meeting*, Dec. 10-13, 2005, Atlanta, Georgia, USA) 106:Abstract 5257, 2005.

Rosenberg et al., "Use of tumor infiltrating lymphocytes and interleukin-2 in the immunotherapy of patients with metastatic melanoma," *New Engl. J. Med.* 319:1676-1680, 1988.

Saudek et al., "A Preliminary Trial of the Programmable Implantable Medication System for Insulin Delivery," *New. Engl. J. Medicine* 321:574, 1989.

Scarpa et al., "Characterization of Recombinant Helper Retrovirus From Moloney-Based Vectors in Ecotropic and Amphotropic Packaging Lines," *Virol.* 180:849-852, 1993.

Sefton, "Implantable pumps," *CRC Crit. Ref Biomed. Eng.* 14:201, 1987.

Siegel et al., "A Phase I/II Study of Xcellerated T Cells™ after Autologous Peripheral Blood Stem Cell Transplantation in Patients with Multiple Myeloma," *Blood (Abstracts of the American Society of Hematology 46th Annual Meeting.* Dec. 4-7, 2004, San Diego, California, USA) 104:Abstract 925, 2004.

Tang et al., "In vitro-expanded antigen-specific regulatory T cells suppress autoimmune diabetes," *J. Exp. Med* 199:1455-1465, 2004.

Taylor et al., "L-Selectinhi but not the L-selectinlo CD4+25+ T-regulatory cells are potent inhibitors of GVHD and BM graft rejection," *Blood (Abstracts of the American Society of Hematology 46th Annual Meeting.* Dec. 4-7, 2004, San Diego, California, USA) 104:Abstract 3804, 2004.

Thompson et al., "A phase I trial of CD3/CD28-activated T cells (Xcellerated T cells) and interleukin-2 in patients with metastatic renal cell carcinoma," *Clin. Cancer. Res.* 9:3562-3570, 2003.

Trenado et al., "Ex vivo-expanded CD4+CD25+ immunoregulatory T cells prevent graft-versus-hostdisease by inhibiting activation/differentiation of pathogenic T cells," *J. Immunol.* 176:1266-1273, 2006.

van Rijn et al., "Quantitative assessment of human T lymphocytes in RAG2(−/−)gammac(−/−) mice: the impact of ex vivo manipulation on in vivo functionality," *Exp. Hematol.* 35:117-127, 2007.

Vij et al., "A Phase I/II Study of Xcellerated T Cells™ after Autologous Peripheral Blood Stem Cell Transplantation in Patients with Multiple Myeloma," *Blood (Abstracts of the American Society of Hematology 45th Annual Meeting.* Dec. 6-9, 2003. San Diego, California, USA) 102:Abstract 139, 2003.

Wierda et al., "A Phase I/II trial of CD3/CD28 activated T cells in patients with chronic lymphocytic leukemia (CLL)," *Journal of Clinical Oncology*, 2004 ASCO Annual Meeting Proceedings (Post-Meeting Edition) vol. 22, No. 14S (Jul. 15 Supplement), 2004:2566.

Xia et al., "Targeting acute allograft rejection by immunotherapy with ex vivo-expanded natural CD4+ CD25+ regulatory T cells," *Transplantation* 82:1749-1755, 2006.

\* cited by examiner

Expansion of CMV-peptide Stimulated CD8+ T Cells Improved with Low Antibody Ratios & Anti-4-1BB Antibody

GENERATION AND ISOLATION OF ANTIGEN-SPECIFIC T CELLS

CROSS-REFERENCE TO RELATED APPLICATION

This application is a division of U.S. patent application Ser. No. 10/742,622, filed Dec. 19, 2003, now pending; which claims the benefit under 35 U.S.C. §119(e) of U.S. Provisional Patent Application No. 60/469,122 filed May 8, 2003. These applications are incorporated herein by reference in their entireties.

BACKGROUND OF THE INVENTION

1. Technical Field

The present invention relates generally to methods for generating, isolating, and expanding antigen-specific T cells. The present invention also relates to compositions of antigen-specific T cells.

2. Description of Related Art

The identification of antigens recognized by T cells in a variety of cancers and infectious diseases has contributed significantly to the interest in the use of antigen-specific immunotherapy for the treatment of malignancies and infectious diseases. Adoptive therapy using antigen-specific T cells represents a conceptually attractive strategy by providing a means to manipulate the specificity, phenotype and magnitude of the intended immune response. Methods to routinely and reproducibly expand antigen-specific T cell clones for use in clinical trials of adoptive therapy would be desirable. Current technologies for generating therapeutic doses of antigen-specific T cells remain limited and could be improved by simplifying the manufacturing process while maintaining or perhaps improving the function of the infused T cells.

The various techniques available for expanding human T-cells have relied primarily on the use of accessory cells (primarily antigen presenting cells (APC)) and/or exogenous growth factors, such as interleukin-2 (IL-2). IL-2 has been used together with an anti-CD3 antibody to stimulate T-cell proliferation, predominantly expanding the $CD8^+$ subpopulation of T-cells. Both APC signals are thought to be required for optimal T-cell activation, expansion, and long-term survival of the T-cells upon re-infusion. The requirement for MHC-matched APCs as accessory cells presents a significant problem for long-term culture systems because APCs are relatively short-lived. Therefore, in a long-term culture system, APCs must be continually obtained from a source and replenished. The necessity for a renewable supply of accessory cells is problematic for treatment of immunodeficiencies in which accessory cells are affected. In addition, when treating viral infection, if accessory cells carry the virus, the cells may contaminate the entire T-cell population during long-term culture.

Further, similar syStems require vaccination with antigen (e.g. tumor/viral antigen), pulsing of antigen-presenting cells with antigens followed by infusion of cells. Expansion of antigen-specific T cells to generate large numbers of antigen-specific T cells often requires labor intensive and expensive cloning, and/or multiple rounds of activation/expansion to achieve therapeutically relevant T cell numbers.

Therefore, there is a need in the art for improved methods to routinely and reproducibly expand antigen-specific T cell clones for use in clinical trials of adoptive therapy and for a simplified manufacturing process that maintains or even improves the function of the antigen-specific T cells.

The present invention provides methods to generate an increased number of highly responsive antigen-specific T cells that have surface receptor and cytokine production characteristics that are more desirable than other expansion methods. The instant invention does not require knowledge of a particular antigen (although known antigens can be used in the context of this invention) and provides for a single, or double, round of expansion to achieve a therapeutically relevant dose of antigen-specific T cells, both of the CD4 and CD8 lineage (and either may be selected if desired).

SUMMARY OF THE INVENTION

Generally, the present invention relates to methods for activating, stimulating and isolating antigen-specific T cells. The present invention also relates to compositions of antigen-specific T cells and methods of their use in the treatment and prevention of cancer, infectious diseases, autoimmune diseases, immune disfunction related to aging, or any other disease state where antigen-specific T cells are desired for treatment.

In one aspect of the present invention, a method for expanding a population of antigen-specific T cells is provided, comprising contacting a population of cells wherein at least a portion thereof comprises antigen-specific T cells, with a surface, wherein said surface has attached thereto a first agent and a second agent, wherein said first agent ligates a CD3/TCR complex on said T cells and said second agent ligates an accessory molecule on said T cells, and wherein said ligation by said first and second agent of said T cells induces proliferation of antigen-specific T cells and wherein said surface is present in a ratio of surface to T cells of 1:2 or less. In certain embodiments the ratio of surface to T cells is between about 1:1 and about 1:50 and any ratio therebetween. In certain embodiments the ratio of surface to T cells is from about 1:2, 1:2.5, 1:5, 1:10, 1:25, 1:50, 1:75, 1:100, or lower. In one embodiment, the surface includes but is not limited to paramagnetic beads, lipids, and cell surfaces. In certain embodiments, the surface comprises paramagnetic beads conjugated to one or more antibodies. In certain embodiments, the surface can have 1, 2, 3, 4, or more antibodies or natural ligands conjugated thereto.

Another aspect of the present invention provides a method for generating antigen-specific T cells comprising exposing a first population of cells wherein at least a portion thereof comprises antigen presenting cells (APC) to a surface wherein said surface has antigen attached thereto, such that said surface with antigen attached thereto is ingested by said APC; exposing a second population of cells wherein at least a portion thereof comprises T cells to the population of cells in part (a); thereby generating antigen-specific T cells. Antigen may be attached or coupled to, or integrated into a surface by a variety of methods known and available in the art and described herein. In one embodiment, the antigen is crosslinked to said surface. In a further embodiment, the attachment to said surface is by covalent or noncovalent, electrostatic, or hydrophobic and may be accomplished by a variety of attachment means, including for example, chemical, mechanical, enzymatic, electrostatic, or other means whereby the antigen(s) is capable of stimulating the cells. For example, the antibody to an antigen first may be attached to a surface, or avidin or streptavidin may be attached to the surface for binding to a biotinylated antigen. The antibody to the ligand may be attached to the surface via an anti-idiotype antibody. Another example includes using protein A or protein G, or other non-specific antibody binding molecules, attached to surfaces to bind an antibody. Alternatively, antigen may be attached to the surface by chemical means, such as cross-linking to the surface, using commercially available cross-linking reagents (Pierce, Rockford, Ill.) or other means. In certain embodiments, antigens are covalently bound to the surface. Further, in one embodiment, commercially available tosyl-activated DYNABEADS™ or DYNABEADS™ with epoxy-surface reactive groups are incubated with the polypeptide antigen of interest according to the manufacturer's instructions. Briefly, such conditions typically involve incubation in a phosphate buffer from pH 4 to pH 9.5 at temperatures ranging from 4 to 37 degrees C.

In one embodiment, the APC are in direct contact with the antigen-specific T cells. In a further embodiment, the APC that are in direct contact with said antigen-specific T cells are isolated by exposing said APC to a magnetic field, wherein said surface comprises a paramagnetic, magnetic, or magnetizable component. In another embodiment, the antigen-specific T cells are expanded by exposing said T cells to a surface wherein said surface has attached thereto a first agent that ligates a first T cell surface moiety of a T cell, and the same or a second surface has attached thereto a second agent that ligates a second moiety of said T cell, wherein said ligation by the first and second agent induces proliferation (expansion) of said antigen-specific T cells. In certain embodiments, at least one agent is an antibody or an antibody fragment. In other embodiments, the first agent is an antibody or a fragment thereof, and the second agent is an antibody or a fragment thereof. In yet another embodiment, the first and the second agents are different antibodies. In certain embodiments, the first agent is an anti-CD3 antibody, an anti-CD2 antibody, or an antibody fragment of an anti-CD3 or anti-CD2 antibody and the second the second agent is an anti-CD28 antibody or antibody fragment thereof. In another embodiment, the first agent is an anti-CD3 antibody and the second agent is an anti-CD28 antibody. In further embodiments, the anti-CD3 antibody and the anti-CD28 antibody are present at a ratio of about 1:1 to about 1:100. In a further embodiment, the antigen-specific T cells are expanded by exposing said antigen-specific T cells to a mitogen, such as phytohemagglutinin (PHA), phorbol myristate acetate (PMA) and ionomycin, lipopolysaccharide (LPS), and superantigen.

In a further embodiment, the antigen of the present invention includes but is not limited to protein, glycoprotein, peptides, antibody/antigen complexes, whole tumor or virus-infected cells, fixed tumor or virus-infected cells, heat-killed tumor or virus-infected cells, tumor lysate, virus lysate, non-soluble cell debris, apoptotic bodies, necrotic cells, whole tumor cells from a tumor or a cell line that have been treated such that they are unable to continue dividing, allogeneic cells that have been treated such that they are unable to continue dividing, irradiated tumor cells, irradiated allogeneic cells, natural or synthetic complex carbohydrates, lipoproteins, lipopolysaccharides, transformed cells or cell line, transfected cells or cell line, transduced cells or cell line, and virally infected cells or cell line. In certain embodiments, antigen is attached to said surface by an antibody/ligand interaction. An antibody/ligand interaction includes but is not limited to an interaction between an antibody/ligand pair selected from the group consisting of anti-MART-1 antibody/MART-1 antigen, anti-WT-1 antibody/WT-1, anti-PR1 antibody/PR1, anti-PR3 antibody/PR3, anti-tyrosinase antibody/tyrosinase antigen, anti-MAGE-1 antibody/MAGE-1 antigen, anti-MUC-1 antibody/MUC-1 antigen, anti-α-fetoprotein antibody/α-fetoprotein antigen, anti-Her2Neu antibody/Her2Neu, anti-HIV gp120 antibody/HIV gp120, anti-influenza HA antibody/influenza HA, anti-CMV pp65/CMV pp65, anti-hepatitis C antibody/hepatitis C proteins, anti-EBV EBNA 3B antibody/EBV EBNA 3B antigen, and anti-human Ig heavy and light chains/Ig from a myeloma cancer patient, and anti-human Ig heavy and light chains/Ig from a CLL cancer patient. In certain embodiments, the antigen is chemically attached to a surface. In one embodiment, the attachment of said antigen to said surface comprises a biotin-avidin interaction. In a further embodiment, the population of cells wherein at least a portion thereof comprises APC is derived from a source selected from the group consisting of a leukapheresis product, peripheral blood, lymph node, tonsil, thymus, tissue biopsy, tumor, spleen, bone marrow, cord blood, $CD34^+$ cells, monocytes, and adherent cells.

Another aspect of the present invention provides a method for generating and expanding antigen-specific T cells comprising exposing a first population of cells wherein at least a portion thereof comprises antigen presenting cells to antigen such that said antigen is taken up by said APC; exposing a second population of cells wherein at least a portion thereof comprises T cells to the population of cells in part (a); thereby generating antigen-specific T cells; and exposing said antigen-specific T cells of part (b) to a surface wherein said surface has attached thereto a first agent that ligates a first T cell surface moiety of a T cell, and the same or a second surface has attached thereto a second agent that ligates a second moiety of said T cell, wherein said ligation by the first and second agent induces proliferation (expansion) of said antigen-specific T cells. In certain embodiments, at least one agent is an antibody or an antibody fragment. In other embodiments, the first agent is an antibody or a fragment thereof, and the second agent is an antibody or a fragment thereof. In yet another embodiment, the first and the second agents are different antibodies. In certain embodiments, the first agent is an anti-CD3 antibody, an anti-CD2 antibody, or an antibody fragment of an anti-CD3 or anti-CD2 antibody and the second the second agent is an anti-CD28 antibody or antibody fragment thereof. In another embodiment, the first agent is an anti-CD3 antibody and the second agent is an anti-CD28 antibody. In further embodiments, the anti-CD3 antibody and the anti-CD28 antibody are present at a ratio of about 1:1 to about 1:100. In one embodiment said antigen-specific T cells are isolated by contacting said T cells with antibodies specific for T cell activation markers. In another embodiment said antibodies are selected from the group consisting of anti-CD25, anti-CD54, anti-CD69, anti-CD38, anti-CD45RO, anti-CD49d, anti-CD40L, anti-CD137, anti-CD62L, and anti-CD134.

A further aspect of the present invention provides a population of antigen-specific T cells generated according to any one of the methods described herein.

An additional aspect of this invention is a composition comprising the antigen-specific T cells according to any of the methods described herein and a pharmaceutically acceptable excipient.

A further aspect of the present invention provides methods for stimulating an immune response in a mammal comprising, administering to the mammal compositions comprising the antigen-specific T cells of the present invention.

An additional aspect of the invention provides for reducing the presence of cancer cells in a mammal comprising, exposing the cancer cells to the compositions comprising antigen-specific T cells. In one embodiment, the cancer cells are from a cancer selected from the group consisting of melanoma, non-Hodgkin's lymphoma, Hodgkin's disease, leukemia, plasmocytoma, sarcoma, glioma, thymoma, breast cancer, prostate cancer, colo-rectal cancer, kidney cancer, renal cell carcinoma, pancreatic cancer, esophageal cancer, brain cancer, lung cancer, ovarian cancer, cervical cancer, multiple myeloma, hepatoma, acute lymphoblastic leukemia (ALL), acute myelogenous leukemia (AML), chronic myelogenous leukemia (CML), and chronic lymphocytic leukemia (CLL).

One aspect of the present invention provides a method for inhibiting the development of a cancer in a mammal, comprising administering to the mammal the composition comprising antigen-specific T cells for the present invention. In certain embodiments, the cancer cells are from a cancer selected from the group consisting of melanoma, non-Hodgkin's lymphoma, Hodgkin's disease, leukemia, plasmocytoma, sarcoma, glioma, thymoma, breast cancer, prostate cancer, colo-rectal cancer, kidney cancer, renal cell carcinoma, pancreatic cancer, esophageal cancer, brain cancer, lung cancer, ovarian cancer, cervical cancer, multiple myeloma, hepatoma, acute lymphoblastic leukemia (ALL), acute myelogenous leukemia (AML), chronic myelogenous leukemia (CML), and chronic lymphocytic leukemia (CLL).

A further aspect of the present invention provides a method for ameliorating an immune response dysfunction in a mammal comprising administering to the mammal the compositions comprising antigen-specific T cells generated using any one of the methods described herein.

Yet another aspect of the invention provides a method for reducing the presence of an infectious organism in a mammal comprising, administering to the mammal a composition comprising antigen-specific T cells generated using any one of the methods described herein. Within this context, an infectious organism can include but is not limited to a virus, a single-stranded RNA virus, a single-stranded DNA virus, a double-stranded DNA virus, Human Immunodeficiency Virus (HIV), Hepatitis A, B, or C virus, Herpes Simplex Virus (HSV), Human Papilloma Virus (HPV), Cytomegalovirus (CMV), Epstein-Barr virus (EBV), a parasite, a bacterium, *M. tuberculosis, Pneumocystis carinii, Candida, Aspergillus*.

An additional aspect of the present invention provides a method for inhibiting the development of an infectious disease in a mammal, comprising administering to the mammal the compositions comprising antigen-specific T cells generated using any one of the methods described herein. In this regard an infectious disease can be caused by an infectious organism including but not limited to a virus, an RNA virus, a DNA virus, Human Immunodeficiency Virus (HIV), Hepatitis A, B, or C virus, Herpes Simplex Virus (HSV), Human Papilloma Virus (HPV), Cytomegalovirus (CMV), Epstein-Barr virus (EBV), a parasite, a bacterium, *M. tuberculosis, Pneumocystis carinii, Candida, Aspergillus*.

DETAILED DESCRIPTION OF THE INVENTION

Figure 1:
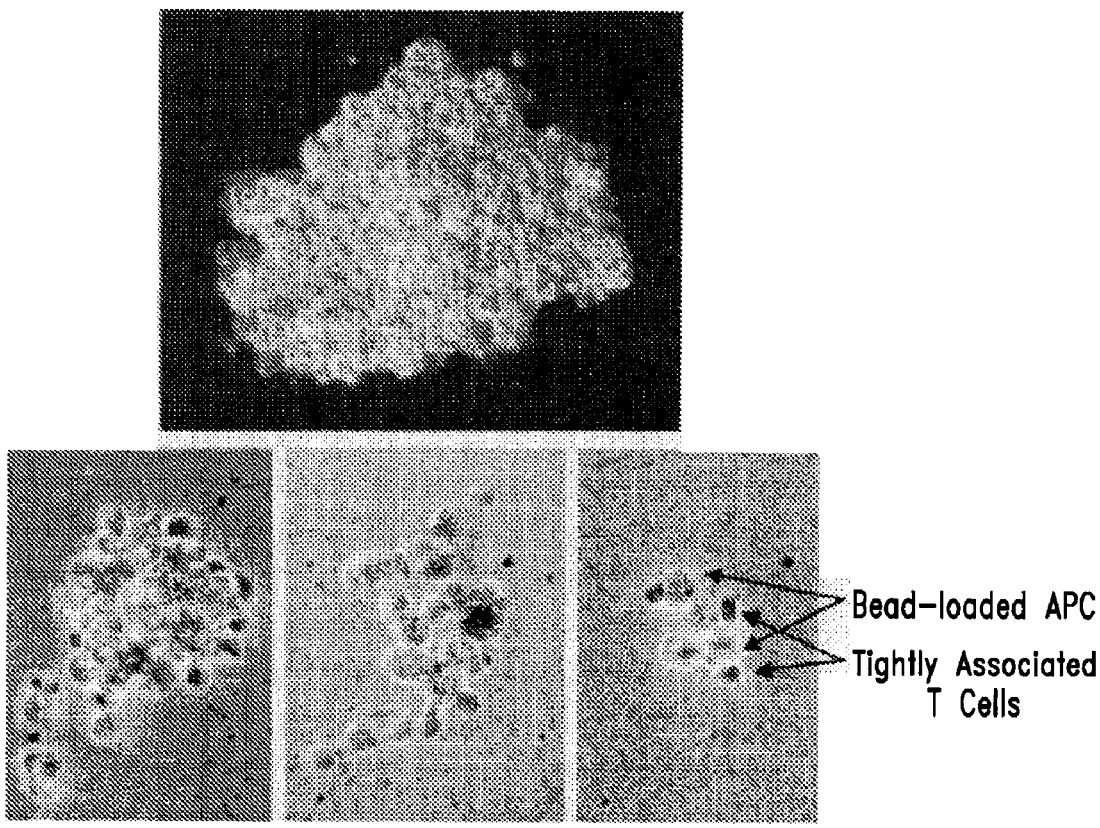
FIG. 1 is a photograph showing the tight association of antigen-specific T cells and bead-loaded antigen presenting cells (APC) post magnetic separation.

Prior to setting forth the invention, it may be helpful to an understanding thereof to set forth definitions of certain terms that will be used hereinafter.

The term "biocompatible", as used herein, refers to the property of being predominantly non-toxic to living cells.

The term "stimulation", as used herein, refers to a primary response induced by ligation of a cell surface moiety. For example, in the context of receptors, such stimulation entails the ligation of a receptor and a subsequent signal transduction event. With respect to stimulation of a T-cell, such stimulation refers to the ligation of a T-cell surface moiety that in one embodiment subsequently induces a signal transduction event, such as binding the TCR/CD3 complex. Further, the stimulation event may activate a cell and upregulate or down-regulate expression or secretion of a molecule, such as down-regulation of TGF-β. Thus, ligation of cell surface moieties, even in the absence of a direct signal transduction event, may result in the reorganization of cytoskeletal structures, or in the coalescing of cell surface moieties, each of which could serve to enhance, modify, or alter subsequent cell responses.

The term "activation", as used herein, refers to the state of a cell following sufficient cell surface moiety ligation to induce a noticeable biochemical or morphological change. Within the context of T-cells, such activation, refers to the state of a T-cell that has been sufficiently stimulated to induce cellular proliferation. Activation of a T-cell may also induce cytokine production and performance of regulatory or cytolytic effector functions. Within the context of other cells, this term infers either up or down regulation of a particular physico-chemical process.

The term "target cell", as used herein, refers to any cell that is intended to be stimulated by cell surface moiety ligation.

An "antibody", as used herein, includes both polyclonal and monoclonal antibodies; primatized (e.g., humanized); murine; mouse-human; mouse-primate; and chimeric; and may be an intact molecule, a fragment thereof (such as scFv, Fv, Fd, Fab, Fab' and F(ab)'$_2$ fragments), or multimers or aggregates of intact molecules and/or fragments; and may occur in nature or be produced, e.g., by immunization, synthesis or genetic engineering; an "antibody fragment," as used herein, refers to fragments, derived from or related to an antibody, which bind antigen and which in some embodiments may be derivatized to exhibit structural features that facilitate clearance and uptake, e.g., by the incorporation of galactose residues. This includes, e.g., F(ab), F(ab)'$_2$, scFv, light chain variable region ($V_L$), heavy chain variable region ($V_H$), and combinations thereof.

The term "protein", as used herein, includes proteins, polypeptides and peptides; and may be an intact molecule, a fragment thereof, or multimers or aggregates of intact molecules and/or fragments; and may occur in nature or be produced, e.g., by synthesis (including chemical and/or enzymatic) or genetic engineering.

The term "agent", "ligand", or "agent that binds a cell surface moiety", as used herein, refers to a molecule that binds to a defined population of cells. The agent may bind any cell surface moiety, such as a receptor, an antigenic determinant, or other binding site present on the target cell population. The agent may be a protein, peptide, antibody and antibody fragments thereof, fusion proteins, synthetic molecule, an organic molecule (e.g., a small molecule), or the like. Within the specification and in the context of T-cell stimulation, antibodies are used as a prototypical example of such an agent.

The terms "agent that binds a cell surface moiety" and "cell surface moiety", as used herein, are used in the context of a ligand/anti-ligand pair. Accordingly, these molecules should be viewed as a complementary/anti-complementary set of molecules that demonstrate specific binding, generally of relatively high affinity (an affinity constant, $K_a$, of about $10^6$ $M^{-1}$ or tighter).

"Antigen-presenting cell (APC)", as used herein, refers to those cells that normally initiate the responses of naïve and/or memory T cells to antigen. In this regard, APC refers to any cell capable of antigen presentation. APCs include, but are not limited to, dendritic cells, monocytes, macrophages, and B cells. An APC may express high levels of MHC class II, ICAM-1 and B7-2.

A "co-stimulatory signal", as used herein, refers to a signal, which in combination with a primary signal, such as TCR/CD3 ligation, leads to T-cell proliferation.

A "ligand/anti-ligand pair", as used herein, refers to a complementary/anti-complementary set of molecules that demonstrate specific binding, generally of relatively high affinity (an affinity constant, $K_a$, of at least about $10^6$ $M^{-1}$). The skilled artisan would understand that this affinity is illustrative only and that affinity constants of the ligand/anti-ligand pairs useful in the context of the present invention might be lower or in some cases higher. For example, in the case of biotin/streptavidin, the streptavidin on-rate is comparable to that of monomeric avidin while its off-rate is seven times lower. The dissociation constant was determined to be $1.3 \times 10(-8)$ M. Exemplary ligand/anti-ligand pairs enzyme/inhibitor, hapten/antibody, lectin/carbohydrate, ligand/receptor, and biotin/avidin or streptavidin. Within the context of the present invention specification receptors and other cell surface moieties are anti-ligands, while agents (e.g., antibodies and antibody fragments) reactive therewith are considered ligands.

"Separation", as used herein, includes any means of substantially purifying one component from another (e.g., by filtration, magnetic attraction, etc.).

"Quiescent", as used herein, refers to a cell state wherein the cell is not actively proliferating.

A "surface", as used herein, refers to any surface capable of having an agent attached thereto and includes, without limitation, metals, glass, plastics, co-polymers, colloids, lipids, cell surfaces, and the like. Essentially any surface that is capable of retaining an agent bound or attached thereto. A prototypical example of a surface used herein, is a particle such as a bead. As such, the terms "surface" and "particle" are used herein interchangeably.

"Immune response or responsiveness" as used herein, refers to activation of cells of the immune system, including but not limited to, T-cells, such that a particular effector function(s) of a particular cell is induced. Effector functions may include, but are not limited to, proliferation, secretion of cytokines, secretion of antibodies, expression of regulatory and/or adhesion molecules, and the ability to induce cytolysis.

"Stimulating an immune response" as used herein, refers to any stimulation such that activation and induction of effector functions of cells of the immune system are achieved.

"Immune response dysfunction" as used herein, refers to the inappropriate activation and/or proliferation, or lack thereof, of cells of the immune system, and/or the inappropriate secretion, or lack thereof, of cytokines, and/or the inappropriate or inadequate induction of other effector functions of cells of the immune system, such as expression of regulatory, adhesion, and/or homing receptors, and the induction of cytolysis.

The terms "preventing" or "inhibiting" the development of a cancer or cancer cells" as used herein, refers to the occurrence of the cancer being prevented or the onset of the cancer being delayed.

The term "treating" or "reducing the presence of a cancer or cancer cells" as used herein, means that the cancer growth is inhibited, which is reflected by, e.g., tumor volume or numbers of malignant cells. Tumor volume may be determined by various known procedures, e.g., obtaining two dimensional measurements with a dial caliper.

"Preventing or inhibiting the development of an infectious disease" as used herein, means the occurrence of the infectious disease is prevented or the onset of the infectious disease is delayed, or the spread of an existing infection is reversed.

"Ameliorate" as used herein, is defined as: to make better; improve (The American Heritage College Dictionary, $3^{rd}$ Edition, Houghton Mifflin Company, 2000).

"Particles" as used herein, may include a colloidal particle, a microsphere, nanoparticle, a bead, or the like. In the various embodiments, commercially available surfaces, such as beads or other particles, are useful (e.g., Miltenyi Particles, Miltenyi Biotec, Germany; Sepharose beads, Pharmacia Fine Chemicals, Sweden; DYNABEADS™, Dynal Inc., Oslo, Norway; PURABEADS™, Prometic Biosciences, magnetic beads from Immunicon, Huntingdon Valley, Pa., microspheres from Bangs Laboratories, Inc., Fishers, Ind.).

"Paramagnetic particles" as used herein, refer to particles, as defined above, that localize in response to a magnetic field.

"Antigen" as used herein, refers to any molecule 1) capable of being specifically recognized, either in its entirety or fragments thereof, and bound by the "idiotypic" portion (antigen-binding region) of a mAb or its derivative; 2) containing peptide sequences which can be bound by MHC and then, in the context of MHC presentation, can specifically engage its cognate T cell antigen receptor.

To "load" an APC with antigen, as used herein, refers to exposing an APC to antigen or antigenic peptide for a period of time sufficient for the APC to uptake, process, and present the antigen, bound by MHC molecules, to T cells. In some cases, the antigen, especially peptide, can be bound by MHC molecules and presented to T cells without being taken up and processed by the APC.

The term "animal" or "mammal" as used herein, encompasses all mammals, including humans. Preferably, the animal of the present invention is a human subject.

The term "exposing" as used herein, refers to bringing into the state or condition of immediate proximity or direct contact.

The term "lysate" as used herein, refers to the supernatant and non-soluble cell debris resulting from lysis of cells. A skilled artisan will recognize that any number of lysis buffers known in the art may be used (see for example Current Protocols in Immunology, John Wiley & Sons, New York. N.Y.).

Cell lysis may also be carried out by freeze-thaw procedures or other means (e.g. sonication, etc.).

The term "apoptotic body" as used herein, is defined as the smaller, intact, membrane-bound fragments that result from apoptotic cells.

The term "proliferation" as used herein, means to grow or multiply by producing new cells.

The term "infectious disease" as used herein, refers to any disease that is caused by an infectious organism. Infectious organisms may comprise viruses, (e.g., RNA viruses, DNA viruses, human immunodeficiency virus (HIV), hepatitis A, B, and C virus, herpes simplex virus (HSV), cytomegalovirus (CMV) Epstein-Barr virus (EBV), human papilloma virus (HPV)), parasites (e.g., protozoan and metazoan pathogens such as *Plasmodia* species, *Leishmania* species, *Schistosoma* species, *Trypanosoma* species), bacteria (e.g., *Mycobacteria*, in particular, *M. tuberculosis, Salmonella*, Streptococci, *E. coli*, Staphylococci), fungi (e.g., *Candida* species, *Aspergillus* species), *Pneumocystis carinii*, and prions (known prions infect animals to cause scrapie, a transmissible, degenerative disease of the nervous system of sheep and goats, as well as bovine spongiform encephalopathy (BSE), or "mad cow disease", and feline spongiform encephalopathy of cats. Four prion diseases known to affect humans are (1) kuru, (2) Creutzfeldt-Jakob Disease (CJD), (3) Gerstmann-Straussler-Scheinker Disease (GSS), and (4) fatal familial insomnia (FFI)). As used herein "prion" includes all forms of prions causing all or any of these diseases or others in any animals used—and in particular in humans and domesticated farm animals.

Sources of T Cells

T cells can be obtained from a number of sources, including peripheral blood mononuclear cells, bone marrow, thymus, tissue biopsy, tumor, lymph node tissue, gut associated lymphoid tissue, mucosa associated lymphoid tissue, spleen tissue, or any other lymphoid tissue, and tumors. T cells can be obtained from T cell lines and from autologous or allogeneic sources. T cells may also be obtained from a xenogeneic source, for example, from mouse, rat, non-human primate, and pig.

Preferably, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis or leukapheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge (for example, the Cobe 2991 cell processor, Baxter) according to the manufacturer's instructions. After washing, the cells may be resuspended in a variety of biocompatible buffers, such as, for example, $Ca^{++}/Mg^{++}$ free PBS. Alternatively, the undesirable components of the apheresis sample may be removed and the cells directly resuspended in culture media.

In another embodiment, T cells are isolated from peripheral blood lymphocytes by lysing the red blood cells and by centrifugation through a PERCOLL™ gradient. A specific subpopulation of T cells, such as $CD28^+$, $CD4^+$, $CD8^+$, $CD45RA^+$, and $CD45RO^+$ T cells, can be further isolated by positive or negative selection techniques. For example, $CD3^+$, $CD28^+$ T cells can be positively selected using CD3/CD28 conjugated magnetic beads (e.g., DYNABEADS® M-450 CD3/CD28 T Cell Expander). In one aspect of the present invention, enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8.

Another method for preparing T cells for stimulation is to freeze the cells after the washing step, which does not require the monocyte-removal step. Wishing not to be bound by theory, the freeze and subsequent thaw step provides a more uniform product by removing granulocytes and, to some extent, monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80° C. at a rate of 1° per minute and stored in the vapor phase of a liquid nitrogen storage tank.

Sources of Antigen-Presenting Cells (APC)

The source of antigen-presenting cell (APC) is typically a tissue source comprising APC or APC precursors that are capable of proliferating and maturing in vitro into professional APC (pAPC) when loaded with antigen and/or treated with the necessary cytokines or factors. "Professional APC" (pAPC) or "antigen-presenting cell" (APC), as used herein, refers to those cells that normally initiate the responses of naïve and/or memory T cells to antigen. Professional APCs include, but are not limited to, DC, macrophages, and B cells. pAPC may express high levels of MHC class II, ICAM-1 and B7-2. In one aspect, APC precursor cells are capable of proliferating and maturing in vitro into dendritic cells (DC). While many tissue sources may be used, typical tissue sources comprise spleen, thymus, tissue biopsy, tumor, afferent lymph, lymph nodes, bone marrow, apheresis or leukapheresis product, and/or peripheral blood. In certain embodiments, apheresis product, bone marrow and peripheral blood are preferred sources. Fetal tissue, fetal or umbilical cord blood, which is also rich in growth factors may also be used as a source of blood for obtaining APC and/or precursor APC. Exemplary precursor cells may be, but are not limited to, embryonic stem cells, $CD34^+$ cells, monocyte progenitors, monocytes, and pre-B cells.

Further, according to one aspect of the present invention, APC may be derived from precursor cells comprising monocytes or $CD34^+$ cells.

In one aspect of the present invention, the source of APC and/or precursor APC is an apheresis or leukapheresis product. Cells are collected using apheresis procedures known in the art. See, for example, Bishop et al., Blood, vol. 83, No. 2, pp. 610-616 (1994). Briefly, cells are collected using conventional devices, for example, a Haemonetics Model V50 apheresis device (Haemonetics, Braintree, Mass.). Apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In another embodiment of the invention, the cells are washed with phosphate buffered saline (PBS). In an alternative embodiment, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge (for example, the Cobe 2991 cell processor, Gambro BCT, Lakewood, Colo.) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

When blood is used as a source of APC, blood leukocytes may be obtained using conventional methods that maintain their viability. According to one aspect of the invention, blood is diluted into medium (preferably RPMI) that may or may not contain heparin (about 100 U/ml) or other suitable anticoagulant. The volume of blood to medium is about 1 to 1. Cells are concentrated by centrifugation of the blood in medium at about 1000 rpm (150 g) at 4° C. Platelets and red blood cells are depleted by resuspending the cells in any number of solutions known in the art that will lyse erythrocytes, for example ammonium chloride. For example, the mixture may be medium and ammonium chloride (at a final concentration of about 0.839 percent) at about 1:1 by volume. Cells may be concentrated by centrifugation and washed in the desired solution until a population of leukocytes, substantially free of platelets and red blood cells, is obtained, typically about two times. Any isotonic solution commonly used in tissue culture may be used as the medium for separating blood leukocytes from platelets and red blood cells. Examples of such isotonic solutions are phosphate buffered saline, Hanks balanced salt solution, or complete growth media including for example RPMI 1640, DMEM, MEM, HAMS F-12, X-Vivo 15, or X-Vivo 20. APC and/or APC precursor cells may also purified by elutriation, using, for example, a Beckman J6ME centrifuge equipped with a J5.0 rotor and a 40 ml elutriation chamber.

In one embodiment of the present invention, isolation of APC and/or precursor APC is performed by preincubating ficolled whole blood or apheresed peripheral blood with one or more varieties of irrelevant or non-antibody coupled paramagnetic particles (approx. 1 vial of beads or $4 \times 10^9$ beads to one batch of cells (typically from about $5 \times 10^8$ to about $2 \times 10^{10}$ cells) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of isolation can be monitored by a variety of methodologies known to those of ordinary skill in the art, including flow cytometric analysis of cells before and after said isolation.

APC obtained from treatment of the tissue source may be cultured to form a primary culture in an appropriate culture container or vessel in an appropriate culture medium. In certain embodiments, the culture medium is supplemented with one or more cytokines. According to the present invention, the appropriate culture container or vessel may be any container with tissue culture compatible surface. Examples include various bags (e.g., Lifecell culture bags), flasks, roller bottles, petri dishes and multi-well containing plates made for use in tissue culture. Surfaces treated with a substance, for example collagen or poly-L-lysine, or antibodies specific for a particular cell type to promote cell adhesion may also be used provided they allow for the differential attachment of cells as described below. Surfaces may be also be chemically treated, for example by ionization. Cells are plated at an initial cell density from about $10^5$ to $10^7$ cells/cm$^2$. In one aspect, cells are plated at $10^6$ cells/cm$^2$.

In one embodiment, the primary cultures from the selected tissue source are allowed to incubate at about 37° C. under standard tissue culture conditions of humidity, $CO_2$, and pH until a population of cells has adhered to the substrate sufficiently to allow for the separation of nonadherent cells. Some immature APC in blood initially are nonadherent to plastic, particularly immature DC, in contrast to monocytes, so that the precursors can be separated after overnight culture. Monocytes and fibroblasts are believed to comprise the majority of adherent cells and usually adhere to the substrate within about 30 minutes to about 24 hours. In certain aspects, nonadherent cells are separated from adherent cells between about 1 to 16 hours. Nonadherent cells may be separated at about 1 to 2 hours. Any method which does not dislodge significant quantities of adherent cells may be used to separate the adherent from nonadherent cells. In certain aspects, the cells are dislodged by simple shaking or pipetting. Pipetting is most preferred.

Adherent cells comprising precursor APC (e.g., monocytes) isolated according to the methods of the invention are allowed to incubate at about 37° C. under standard tissue culture conditions of humidity, $CO_2$, and pH until a population of cells has reached an immature APC stage. In certain aspects, according to the present invention, adherent cells are allowed to incubate for a period of between 4 hours and 7 days. However, one of ordinary skill in the art will readily appreciate that incubation times and conditions may vary. "Immature APC" as used herein, refers to an intermediate differentiation state of an APC wherein the APC has the capacity to endocytose or phagocytose antigen, foreign bodies, necrotic and/or apoptosing tissue and/or cells. Immature APC may be CD14$^-$ or CD14$^+$ depending on the origin of the precursor cells. Immature APC may also express CD1a, CD40, CD86, CD54, and intermediate levels of MHC class II (levels of marker expression on sample cells can be compared by flow cytometric analysis to levels of expression on MHC class II-negative cells and cells known to express high levels of MHC class II). Immature APC typically do not express CCR7.

In certain aspects of the present invention, it is not necessary to separate T cells from APC. For example, in one embodiment, PBMC comprising APC and T cells can be exposed to antigen as described herein and the resulting antigen-specific T cells further expanded as described herein.

In certain aspects of the present invention, it is not required that the APCs or the T cells described herein be derived from an autologous source. Thus, the APC and T cells can be obtained from a matched or unmatched donor, or from a cell line, a T cell line, or other cells grown in vitro. Methods for matching haplotypes are known in the art. Furthermore, the APC and T cells or supernatant therefrom may be obtained from a xenogeneic source, for example, mouse, rat, non-human primate, and porcine cells may be used.

Sources of Antigen

According to the present invention, the source of antigen may be, but is not limited to, protein, including glycoprotein, peptides (including pools of overlapping peptides), superantigens (e.g., SEA, SEB, TSST-1) antibody/antigen complexes, tumor lysate, viral lysate (e.g., CMV lysate and the like), non-soluble cell debris, apoptotic bodies, necrotic cells, whole cells which are live, fixed, irradiated, heat-killed or otherwise manipulated, whole tumor cells from a tumor or a cell line that have been treated such that they are unable to continue dividing, allogeneic cells that have been treated such that they are unable to continue dividing, irradiated tumor cells, irradiated allogeneic cells, natural or synthetic complex carbohydrates, lipoproteins, lipopolysaccharides, RNA or a translation product of said RNA, and DNA or a polypeptide encoded by said DNA. Non-transformed cells are typically irradiated with gamma rays in the range of about 3000 to 3600 rads, more preferably at about 3300 rads. Lymphoblastoid or tumor cell lines are typically irradiated with gamma rays in the range of about 6000 to 10,000 rads, more preferably at about 8000 rads. Necrotic and apoptotic cells may be generated by physical, chemical, or biological means. Necrotic cells are typically generated by freeze-thawing, while apoptotic cells are generated using UV irradiation. UV and gamma irradiation, and freeze-thawing procedures are well known in the art and are described, for example, in Current Protocols in Molecular Biology or Current Protocols in Immunology, John Wiley & Sons, New York. N.Y.

Antigen source may also comprise non-transformed, transformed, transfected, or transduced cells or cell lines. Cells may be transformed, transfected, or transduced using any of a variety of expression or retroviral vectors known to those of ordinary skill in the art that may be employed to express recombinant antigens. Expression may also be achieved in any appropriate host cell that has been transformed, transfected, or transduced with an expression or retroviral vector containing a DNA molecule encoding recombinant antigen(s). Any number of transfection, transformation, and transduction protocols known to those in the art may be used, for example those outlined in Current Protocols in Molecular Biology, John Wiley & Sons, New York. N.Y., or in numerous kits available commercially (e.g., Invitrogen Life Technologies, Carlsbad, Calif.). In one embodiment of the present invention, recombinant vaccinia vectors and cells infected with said vaccina vectors, may be used as a source of antigen. Recombinant antigen may include any number of defined tumor antigens described below.

According to certain methods of the invention, antigen may comprise viral antigens such as CMV pp65, HIV pg120, and the like. In certain embodiments, antigen may comprise defined tumor antigens such as the melanoma antigen Melan-A (also referred to as melanoma antigen recognized by T cells or MART-1), melanoma antigen-encoding genes 1, 2, and 3 (MAGE-1, -2, -3), melanoma GP100, carcinoembryonic antigen (CEA), the breast cancer antigen, Her-2/Neu, serum prostate specific antigen (PSA), Wilm's Tumor (WT-1), PR1, PR3 (antigens implicated in the graft-versus-leukemia (GVL) effect in chronic myeloid leukemia), mucin antigens, MUC-1, -2, -3, -4, B cell lymphoma idiotypes, and the like. The skilled artisan would appreciate that any tumor antigen would be useful in the context of the present invention.

Activation of Antigen-Specific T Cells

One aspect of the present invention stems from the surprising finding that using different bead:cell ratios can lead to different outcomes with respect to expansion of antigen-specific T cells. In particular, bead:cell ratios can be varied to selectively expand or delete antigen-specific (memory) T cells. In one embodiment, the particular bead:cell ratio used selectively expands antigen-specific T cells. Thus, in one embodiment of the present invention, antigen-specific T cells are activated by direct contact of a population of cells wherein at least a portion thereof comprises T cells (e.g., a leukapheresis product from an individual, blood sample, tumor biopsy, etc.), with a surface, wherein said surface has attached thereto a first agent that ligates a first T cell surface moiety of a T cell, and the same or a second surface has attached thereto a second agent that ligates a second moiety of said T cell, wherein said ligation by the first and second agent induces proliferation (expansion) of antigen-specific T cells present within the population of cells.

Without being bound by theory, it is thought that the antigen-specific T cells are sensitized to further stimulation. Thus, the key appears to be the strength of the T cell activation signal: selective expansion of memory T cells (antigen-specific T cells) occurs with "weak" signals while selective deletion of memory T cells occurs with "strong" signals. The quantity of the CD3/TCR (and CD28) receptors that are bound by ligands determines the signal strength. Thus, stimulation with high bead:cell ratios provides a high concentration of stimulating antibody (i.e., "strong signal"), leading to overstimulation of antigen-specific T cells, causing them to die, either by apoptosis or other mechanisms. Using lower bead:cell ratios provides a stimulation signal to antigen-specific T cells that does not over-stimulate, but rather induces rapid proliferation of these cells.

In one embodiment of the present invention, antigen-specific T cells are activated by culturing T cells isolated as described herein above, with APC that have been loaded with antigen.

In another embodiment, suitable APC are plated in culture dishes and exposed to a source of antigen as described herein, in a sufficient amount and for a sufficient period of time to allow the antigen to bind and/or be taken up by the APC. In certain aspects, antigen is exposed to the APC for a period of time between 24 hours and 4 days. In one particular embodiment, the antigen is exposed to the APC for 36, 48, or 72 hours. In a further embodiment, the antigen is exposed to the APC for 2.5, 3, 3.5, or 4 days. In certain embodiments, antigen may be exposed to the APC for periods longer than 4 days, for example 4.5, 5, 5.5, 6, 6.5, 7, 7.5, 8, 8.5, 9, 9.5, or 10 days. The amount and time necessary to achieve binding and uptake of the antigen by the APC may differ depending on the source and type of antigen and may be determined by those of ordinary skill in the art by immunoassay or binding assay. Other methods known to those of skill in the art may be used to detect the presence of antigen in the context of MHC on the APC following their exposure to antigen.

In yet an additional embodiment, PBMC (e.g., from blood, a leukapheris product, etc.) from a subject are cultured directly in the presence of antigen, as described herein, to load APC with the antigen and to activate/stimulate antigen-specific T cells present in the PBMC. In this regard, PBMC may be collected from an individual, contacted with an antigen of interest, such as a tumor antigen, or a viral lysate, etc. In this manner, the APC present in the PBMC are loaded with the antigen, which is then presented to the T cells present in the sample. In an additional embodiment, the antigen-specific T cells of the present invention may be stimulated with peptide-MHC tetramers, see for example Altman, et al., Science 1998 Jun. 19; 280(5371):1821.

The APC of the present invention may be loaded with antigen through genetic modification. Genetic modification may comprise RNA or DNA transfection using any number of techniques known in the art, for example electroporation (using e.g., the Gene Pulser II, BioRad, Richmond, Calif.), various cationic lipids, (LIPOFECTAMINE™, Life Technologies, Carlsbad, Calif.), or other techniques such as calcium phosphate transfection as described in Current Protocols in Molecular Biology, John Wiley & Sons, New York. N.Y. For example, 5-50 µg of RNA or DNA in 500 µl of Opti-MEM can be mixed with a cationic lipid at a concentration of 10 to 100 µg, and incubated at room temperature for 20 to 30 minutes. Other suitable lipids include LIPOFECTIN™, LIPOFECTAMINE™. The resulting nucleic acid-lipid complex is then added to $1\text{-}3\times10^6$ cells, preferably $2\times10^6$, antigen-presenting cells in a total volume of approximately 2 ml (e.g., in Opti-MEM), and incubated at 37° C. for 2 to 4 hours. The APC may also be transduced using viral transduction methodologies as described below.

In another embodiment of the present invention, APC are loaded with antigen attached to, coated on, or otherwise immobilized on particles, such as beads. In the various embodiments, commercially available beads or other particles, are useful, e.g., Miltenyi Particles, Miltenyi Biotec, Germany; Sepharose beads, Pharmacia Fine Chemicals, Sweden; DYNABEADS™, Dynal Inc., New York. In certain embodiments, paramagnetic particles or beads are particularly suitable. Such paramagnetic beads or particles are commercially available, for example, those produced by Dynal AS under the trade name Dynabeads™. Exemplary Dynabeads™ in this regard are M-280, M-450, and M-500. In one embodiment, whole cells which are live, fixed, irradiated, heat-killed or otherwise manipulated, are immobilized to ingestible beads, via for example antibody/ligand specific means or chemical means. Similarly, tumor cell or virus-infected cell lysates, or antigen-preparations can be attached or otherwise immobilized to the beads (which may be paramagnetic or otherwise selectable). These coated or antigen/cell/lysate-attached beads can be mixed with human or other animal peripheral blood preparations (or other compositions containing some percentage of antigen-presenting cells (particularly those capable of ingesting particles and then processing and presenting antigens associated with the particles). Phagocytic cells will ingest the beads/particles, process antigens associated with the particles, and present them to T cells in the cell mix. As noted elsewhere herein, only T cells with specificity for the variety of presented antigens will interact in a positive manner with the APC. APC containing paramagnetic or otherwise selectable beads can then be isolated carrying with them antigen-specific T cells.

In one particular embodiment, the particles of the present invention comprise a cell surface, such as described in U.S. patent application Ser. No. 10/336,224, PCT/US03/00339. In this regard, antigen can be attached to the cells via antibody/ligand specific means as described herein or through genetic modification. Any number of transfection, transformation, and transduction protocols known to those in the art may be used, for example those outlined in Current Protocols in Molecular Biology, John Wiley & Sons, New York. N.Y., or in numerous kits available commercially (e.g., Invitrogen Life Technologies, Carlsbad, Calif.). Such techniques may result in stable transformants or may be transient. One suitable transfection technique is electroporation, which may be performed on a variety of cell types, including mammalian cells, yeast cells and bacteria, using commercially available equipment. Optimal conditions for electroporation (including voltage, resistance and pulse length) are experimentally determined for the particular host cell type, and general guidelines for optimizing electroporation may be obtained from manufacturers. Other suitable methods for transfection will depend upon the type of cell used (e.g., the lithium acetate method for yeast), and will be apparent to those of ordinary skill in the art. Following transfection, cells may be maintained in conditions that promote expression of the polynucleotide within the cell. Appropriate conditions depend upon the expression system and cell type, and will be apparent to those skilled in the art.

Antigen may be attached to the particles, such as beads, by antibody/ligand specific means, e.g. through particles, such as beads, conjugated to an antibody or antibodies. Suitable antibody/ligand pairs may include, but are not limited to anti-MART-1 antibody/MART-1 antigen, anti-WT-1 antibody/WT-1, anti-PR1 antibody/PR1, anti-PR3 antibody/PR3, anti-tyrosinase antibody/tyrosinase antigen, anti-MAGE-1 antibody/MAGE-1 antigen, anti-MUC-1 antibody/MUC-1 antigen, anti-α-fetoprotein antibody/α-fetoprotein antigen, anti-Her2Neu antibody/Her2Neu, anti-HIV gp120 antibody/HIV gp120, anti-influenza HA antibody/influenza HA, anti-CMV pp65/CMV pp65, anti-hepatitis C antibody/hepatitis C proteins, anti-EBV EBNA 3B antibody/EBV EBNA 3B antigen, and anti-human Ig heavy and light chains/Ig from cancer patient, such as myeloma or CLL patient. Other protein:protein binding interactions may be suitable for attaching antigen to particles, such as beads, for example, receptor/ligand interactions may be utilized. In certain embodiments, the antigen/protein is attached to the particles, such as beads by chemical means, e.g. antigen/protein can be bound through non-covalent association of the antigen and bead, simply by incubating/contacting the two together for a time and under conditions sufficient for association to occur. In yet further embodiments, antigen may be attached to the particles, such as beads by a biotin/avidin or streptavidin interaction. In certain embodiments, hydrophobic "naked" beads with p-toluenesulphonyl (tosyl) reactive groups are used. Proteins are adsorbed hydrophobically on initial coupling with covalent binding of primary amine groups ($NH_2$) and sulphydryl groups (SH) occurring overnight. Coupling reactions can be performed at neutral pH however high pH and incubation at 37° C. can promote covalent binding.

In certain aspects, T cells isolated from a tissue source are exposed to antigen-loaded APC described herein for a time sufficient for T cells specific for a given antigen to be activated, for example as described in U.S. Pat. No. 5,827,642, or as described in Riddell, et al., 1990, J. Immunol. Methods, 128:189-201. In one embodiment, T cells are exposed to antigen-loaded APC for a period of between about several hours to about 0.5, 1, 2, 3, 4, 5, 6, 7, 8, 9, 10, 11, 12, 13, 14, 15, 16, 17, 18, 19, or about 20 days.

In one embodiment, the T cells are exposed to antigen, or antigen-loaded APC as described herein in vivo. In this regard, antigen or antigen-loaded APC may be administered to an individual in order to stimulate and activate the T cells in vivo. The T cells may then be expanded either in vivo or ex vivo using the methods as described herein, such as with anti-CD3/anti-CD28 beads. The quantity and frequency of administration will be determined by such factors as the condition of the individual, and the type and severity of disease, although appropriate dosages may be determined by clinical trials. In certain embodiments the T cells are exposed to antigen in vivo in an individual prior to onset of a disease or prior to treatment with other known therapies. In this regard, the antigen-specific T cells are generated and then isolated and expanded and preserved for later use.

In one embodiment of the present invention, isolation of antigen-specific T cells in direct contact with APC loaded with antigen immobilized on particles, such as beads, is performed by magnetic isolation of cells which have attached to or engulfed paramagnetic particles. Such separation can be performed using standard methods available in the art. For example, any magnetic separation methodology may be used including a variety of which are commercially available, (e.g., DYNAL® Magnetic Particle Concentrator (DYNAL MPC®), MACS, Miltenyi Biotec, Germany). In this regard, only T cells with specificity for the variety of presented antigens will optimally interact in a positive manner with the APC. APC containing paramagnetic (or otherwise selectable) beads can then be isolated (via magnet or otherwise) carrying with them antigen-specific T cells. These antigen-specific T cells can then be activated/expanded by a variety of means, such as via XCELLERATE™ technologies as described herein and U.S. patent application Ser. Nos. 10/350,305; 10/187,467; 10/133,236; 09/960,264; 09/794,230; PCT/US01/06139; and PCT/US02/28161.

In another embodiment of the invention, antigen-specific T cells are isolated by positive selection. Such isolation can be carried out on T cells freshly isolated from a subject or on T cells that have been exposed to antigen or antigen-loaded APC as described herein. Numerous immunoselection methods known to skilled artisans may be used. Such techniques are described, for example, in Current Protocols in Immunology, John Wiley & Sons, New York. N.Y. Markers that may be useful for the positive selection of antigen-specific cells include, but are not limited to, CD25, CD54, CD69, CD38, CD45RO, CD49d, CD40L, CD137, CD62L, and CD134. In one embodiment, fluorescence activated cell sorting may also be used to isolate desired antigen-specific T cells. In an additional embodiment, antigen-specific T cells may be isolated using peptide-MHC tetramers, see for example Altman, et al., Science 1998 Jun. 19; 280(5371):1821.

In a further embodiment of the invention, antigen-specific T cells may be genetically modified. Genetic modification may comprise RNA or DNA transfection using any number of techniques known in the art, for example electroporation (using e.g., the Gene Pulser II, BioRad, Richmond, Calif.), various cationic lipids, (LIPOFECTAMINE™, Life Technologies, Carlsbad, Calif.), or other techniques such as calcium phosphate transfection as described in Current Protocols in Molecular Biology, John Wiley & Sons, New York. N.Y. For example, 5-50 µg of RNA or DNA in 500 µl of Opti-MEM can be mixed with a cationic lipid at a concentration of 10 to 100 µg, and incubated at room temperature for 20 to 30 minutes. Other suitable lipids include LIPOFECTIN™, LIPOFECTAMINE™. The resulting nucleic acid-lipid complex is then added to $1-3\times10^6$ cells, preferably $2\times10^6$, antigen-presenting cells in a total volume of approximately 2 ml (e.g., in Opti-MEM), and incubated at 37° C. for 2 to 4 hours. The APC may also be transduced using viral transduction methodologies as described below.

The antigen-specific T cells of the present invention may alternatively be genetically modified using retroviral transduction technologies. In one aspect of the invention, the retroviral vector may be an amphotropic retroviral vector, preferably a vector characterized in that it has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. Retroviruses adaptable for use in accordance with the present invention can, however, be derived from any avian or mammalian cell source. These retroviruses are preferably amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

In one aspect of the present invention, genetically modified antigen-specific T cells can be isolated by any one of numerous immunoselection methods known to skilled artisans using antibodies or other receptors/ligands specific for the protein or proteins expressed from the transgene. Such techniques are known in the art, for example, in Current Protocols in Immunology, John Wiley & Sons, New York. N.Y.

In one particular embodiment, the antigen-specific T cells may be genetically modified to express a suicide gene, e.g. the herpes simplex virus thymidine kinase (HSV-TK) as described in Bonini, et al., 1997 Science, 276(5319):1719-24, and/or other surface markers (e.g., truncated nerve growth factor (dNGFR)) for in vivo tracking and/or control of infused antigen-specific T cells. In a further embodiment, the antigen-specific T cells may be genetically modified to express a protein for targeting the T cells to a particular tissue of interest.

Those of ordinary skill in the art will readily appreciate that the cell separation and culture methodologies described herein, may be carried out in a variety of environments (i.e., containers). Examples include various bags (e.g., Lifecell culture bags), flasks, roller bottles, bioreactors, (e.g., CellCube (Corning Science Products) or CELL-PHARM, (CD-Medical, Inc. of Hialeah, Fla.)), petri dishes and multi-well containing plates made for use in tissue culture, or any container capable of holding cells, preferably in a sterile environment. In one embodiment of the present invention a bioreactor is also useful. For example, several manufacturers currently manufacture devices that can be used to grow cells and be used in combination with the methods of the present invention. See for example, Celdyne Corp., Houston, Tex.; Unisyn Technologies, Hopkinton, Mass.; Synthecon, Inc. Houston, Tex.; Aastrom Biosciences, Inc. Ann Arbor, Mich.; Wave Biotech LLC, Bedminster, N.J. Further, patents covering such bioreactors include U.S. Pat. Nos. 6,096,532; 5,985,653; 5,888,807; 5,190,878.

Suitable complete growth media for the culture of the APC and antigen-specific T cells of the present invention include for example RPMI 1640, DMEM, MEM, α-MEM, AIM-V, HAMS F-12, X-Vivo 15, or X-Vivo 20. In further embodiments, the media can comprise a cytokine, such as IL-2, IFN-γ, IL-4, GM-CSF, IL-10, IL-12, TGFβ, and TNF-α, or a vitamin. In further embodiments, the medium comprises surfactant, an antibody, plasmanate or a reducing agent (e.g. N-acetyl-cysteine, 2-mercaptoethanol). The growth medium for the cells at each step of the method of the invention should allow for the survival of the APC and/or the antigen-specific T cells. Any growth medium typically used to culture cells may be used according to the method of the invention provided the medium is supplemented with the appropriate cytokines, serum, antibiotics, vitamins, amino acids or other necessary additives. According to the present invention, the cytokines may be, but are not limited to, granulocyte-macrophage colony-stimulating factor (GM-CSF) and interleukin 4 (IL-4), or IL-13. Other exemplary cytokines and growth factors that may be added to the growth medium include but are not limited to interleukin 1α (IL-1α) and β (IL-1β), IL-2, tumor necrosis factor alpha (TNF-α), interleukin 3 (IL-3), monocyte colony stimulating factor (M-CSF), granulocyte colony-stimulating factor (G-CSF), stem cell factor (SCF), interleukin 6 (IL-6), interleukin 15 (IL-15), and Flt3-ligand. Preferred media include RPMI 1640, AIM-V, DMEM, MEM, α-MEM, F-12, X-Vivo 15, and X-Vivo 20, with added amino acids and vitamins, either serum-free or supplemented with an appropriate amount of serum (or plasma) or a defined set of hormones, and an amount of cytokine(s) sufficient to support the expansion of the antigen-specific T cells. In one aspect, the preferred media comprises 1 liter of X-Vivo 15, BioWhittaker; with 50 ml heat inactivated pooled human serum, 20 ml 1M Hepes, 10 ml 200 mM L-glutamine with or without about 100,000 I.U. IL-2. In one aspect, media may include lipids and/or sources of protein. RPMI 1640 supplemented with 1-5% human AB serum preferred. Mixtures of cytokines may also be used. Cells may also be adapted to grow in other sera, such as fetal calf (bovine) serum (FCS/FBS), at other concentrations of serum, or in serum-free media. For example, serum-free medium supplemented with hormones is also suitable for culturing the APC precursors. Media may, but does not necessarily, contain antibiotics to minimize growth of bacteria in the cultures. Penicillin, streptomycin or gentamicin or combinations containing them are preferred. The medium, or a portion of the medium, in which the cells are cultured should be periodically replenished to provide fresh nutrients including GM-CSF, IL-4, IL-13, IL-15 and/or other cytokines.

Expansion of Antigen-Specific T Cells

Expansion of the antigen-specific T cells of the present invention is carried out by cell surface moiety ligation that re-stimulates the antigen-specific T cells to proliferate. In one embodiment of the present invention, the antigen-specific T cells are first isolated by methods described herein following exposure to antigen loaded APC. In another embodiment of the present invention, the antigen-specific T cells are expanded directly from the culture with antigen-loaded APC present without an isolation step.

In one particular embodiment, antigen-specific T cells are activated and expanded using XCELLERATE™ processes as described herein and in U.S. patent application Ser. Nos. 10/350,305; 10/187,467; 10/133,236; 09/960,264; 09/794,230, with no addition of antigen or antigen-coated particles. In this regard, as noted further herein, antigen-specific T cells that have been previously stimulated or activated in vivo (e.g. memory T cells) are expanded by an agent providing a primary activation signal such as an anti-CD3 antibody and an agent providing a co-stimulatory signal, such as an anti-CD28 antibody, with both agents co-immobilized to the same surface, such as a paramagnetic bead. As further described herein, see in particular the Examples below, varying the bead:cell ratios during this expansion phase, in particular using low bead:cell ratios, favors expansion of antigen-specific T cells. For example, bead to cell ratios of 1:200, 1:150, 1:125, 1:110, 1:100, 1:75, 1:50, 1:25, 1:20, 1:15, 1:10, 1:5 or 1:2.5 are used to expand antigen-specific T cells. A particular advantage of this aspect of the present invention is that it is not necessary to add antigen.

Generally, expansion is carried out by re-stimulating a population of antigen-specific T cells and simultaneously stimulating an accessory molecule on the surface of the antigen-specific T cells with a ligand which binds the accessory molecule, as described for example, in U.S. patent application Ser. Nos. 10/350,305, 10/187,467, 10/133,236, 09/960,264, 09/794,230, 08/253,694, 08/403,253, 08/435,816, 08/592,711, 09/183,055, 09/350,202, and 09/252,150, and U.S. Pat. Nos. 5,858,358; 6,352,694; and 5,883,223.

Generally, re-stimulation may be accomplished by cell surface moiety ligation, such as through the T cell receptor (TCR)/CD3 complex or the CD2 surface protein. A number of anti-human CD3 monoclonal antibodies are commercially available, exemplary are, clone BC3 (XR-CD3; Fred Hutchinson Cancer Research Center, Seattle, Wash.), OKT3, prepared from hybridoma cells obtained from the American Type Culture Collection, and monoclonal antibody G19-4. Similarly, stimulatory forms of anti-CD2 antibodies are known and available. Stimulation through CD2 with anti-CD2 antibodies is typically accomplished using a combination of at least two different anti-CD2 antibodies. Stimulatory combinations of anti-CD2 antibodies that have been described include the following: the T11.3 antibody in combination with the T11.1 or T11.2 antibody (Meuer et al., Cell 36:897-906, 1984), and the 9.6 antibody (which recognizes the same epitope as T11.1) in combination with the 9-1 antibody (Yang et al., J. Immunol. 137:1097-1100, 1986). Other antibodies that bind to the same epitopes as any of the above-described antibodies can also be used. Additional antibodies, or combinations of antibodies, can be prepared and identified by standard techniques. Re-stimulation may also be achieved through contact with antigen, peptide, protein, peptide-MHC tetramers (see Altman, et al Science 1996 Oct. 4; 274(5284): 94-6), superantigens (e.g., Staphylococcus enterotoxin A (SEA), Staphylococcus enterotoxin B (SEB), Toxic Shock Syndrome Toxin 1 (TSST-1)), endotoxin, or through a variety of mitogens, including but not limited to, phytohemagglutinin (PHA), phorbol myristate acetate (PMA) and ionomycin, lipopolysaccharide (LPS), T cell mitogen, and IL-2.

The antigen-specific cell population may be stimulated or restimulated as described herein, such as by contact with an anti-CD3 antibody or an anti-CD2 antibody immobilized on a surface, or by contact with a protein kinase C activator (e.g., bryostatin) in conjunction with a calcium ionophore. For co-stimulation of an accessory molecule on the surface of the T-cells, a ligand that binds the accessory molecule is used. For example, a population of $CD4^+$ cells can be contacted with an anti-CD3 antibody and an anti-CD28 antibody, under conditions appropriate for stimulating proliferation of the T-cells. Similarly, to stimulate proliferation of $CD8^+$ T-cells, an anti-CD3 antibody and the anti-CD28 antibody B-T3, XR-CD28 (Diaclone, Besançon, France) can be used as can other methods commonly known in the art (Berg et al., Transplant Proc. 30(8):3975-3977, 1998; Haanen et al., J. Exp. Med. 190(9): 1319-1328, 1999; Garland et al., J. Immunol. Meth. 227(1-2):53-63, 1999).

To further re-stimulate a population of antigen-specific T cells, a co-stimulatory or accessory molecule on the surface of the T cells, such as CD28, is stimulated with a ligand that binds the accessory molecule. Accordingly, one of ordinary skill in the art will recognize that any agent, including an anti-CD28 antibody or fragment thereof capable of cross-linking the CD28 molecule, or a natural ligand for CD28 can be used to stimulate T cells. Exemplary anti-CD28 antibodies or fragments thereof useful in the context of the present invention include monoclonal antibody 9.3 ($IgG2_a$) (Bristol-Myers Squibb, Princeton, N.J.), monoclonal antibody KOLT-2 (IgG1), 15E8 (IgG1), 248.23.2 (IgM), clone B-T3 (XR-CD28; Diaclone, Besançon, France) and EX5.3D10 ($IgG2_a$) (ATCC HB11373). Exemplary natural ligands include the B7 family of proteins, such as B7-1 (CD80) and B7-2 (CD86) (Freedman et al., J. Immunol. 137:3260-3267, 1987; Freeman et al., J. Immunol. 143:2714-2722, 1989; Freeman et al., J. Exp. Med. 174:625-631, 1991; Freeman et al., Science 262:909-911, 1993; Azuma et al., Nature 366:76-79, 1993; Freeman et al, J. Exp. Med. 178:2185-2192, 1993).

In a further embodiment of the invention, activation of a T-cell population may be enhanced by co-stimulation of other T-cell integral membrane proteins. For example, binding of the T-cell integrin LFA-1 to its natural ligand, ICAM-1, may enhance activation of cells. Another cell surface molecule that may act as a co-stimulator for T-cells is VCAM-1 (CD106)

that binds very-late-antigen-4 (VLA-4) on T-cells. Ligation of 4-1BB (CD137), a co-stimulatory receptor expressed on activated T cells, and/or NKG2D may also be useful in the context of the present invention to amplify T-cell mediated immunity. It should be noted that more than one costimulatory molecule as described herein may be stimulated at a time, and in any combination, such that desired expansion of the T cells occurs.

In addition, binding homologues of a natural ligand, whether native or synthesized by chemical or recombinant techniques, can also be used in accordance with the present invention. Other agents may include natural and synthetic ligands. Agents may include, but are not limited to, other antibodies or fragments thereof, a peptide, polypeptide, growth factor, cytokine, chemokine, glycopeptide, soluble receptor, steroid, hormone, mitogen, such as PHA, or other superantigens.

The primary stimulatory signal and the co-stimulatory signal for the T-cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In a preferred embodiment, the two agents are immobilized on beads, either on the same bead, i.e., "cis," or to separate beads, i.e., "trans." By way of example, the agent providing the primary activation signal is an anti-CD3 antibody and the agent providing the co-stimulatory signal is an anti-CD28 antibody; and both agents are co-immobilized to the same surface, such as a bead, in equivalent molecular amounts. In one embodiment, a 1:1 ratio of each antibody bound to the beads for $CD4^+$ T-cell expansion and T-cell growth is used.

One aspect of the present invention stems from the surprising finding that using lower ratios of anti-CD3:anti-CD28 antibodies bound to the beads results in improved expansion of T cells, including antigen-specific T cells. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 0.5 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e. the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T-cells. As those of ordinary skill in the art can readily appreciate, the ratio of particle to cells may dependant on particle size relative to the target cell. For example, small sized beads could only bind a few cells, while larger beads could bind many. In certain embodiments the ratio of particles to cells ranges from 1:100 to 100:1 and any integer values in-between and in further embodiments the ratio comprises 1:9 to 9:1 and any integer values in between, can also be used to stimulate T-cells. The ratio of anti-CD3- and anti-CD28-coupled particles to T-cells that result in T-cell stimulation and expansion can vary as noted above, however in certain embodiments the ratio may be 1:150 or lower. Certain preferred ratios include 1:150, 1:100, 1:75, 1:50, 1:40, 1:30, 1:25, 1:20, 1:15, 1:10, 1:9, 1:8, 1:7, 1:6, 1:5, 1:4, 1:3, 1:2.5, 1:2, 1:1, 2:1, 3:1, 4:1, 5:1, 6:1, 7:1, 8:1, 9:1, 10:1, 15:1, and 20:1 with one preferred ratio being 1:1 particles per T-cell. In one embodiment, a ratio of particles to cells of 1:1 or less is used. In one particular embodiment, a preferred particle:cell ratio is 1:2.5 or 1:5. In further embodiments, the ratio of particles to cells can be varied depending on the day of stimulation. For example, in one embodiment, the ratio of particles to cells is from 1:5, 1:2.5, 1:1 to 10:1 on the first day and additional particles are added to the cells every day or every other day thereafter for up to 10 days, at final ratios of from 1:1, 1:5, 1:20, 1:25, 1:50, or 1:100 (based on cell counts on the day of addition). In one particular embodiment, the ratio of particles to cells is 1:2.5, 1:5, or 1:1 on the first day of stimulation and adjusted to 1:5 on the third and fifth days of stimulation. In a further embodiment, the ratio of particles to cells is 1:2.5, 1:5, or 1:1 on the first day of stimulation and adjusted to 1:10, 1:20, 1:25, 1:50, or 1:100 at day 5, 7, or 9. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention.

One aspect of the present invention stems from the surprising finding that using different bead:cell ratios can lead to different outcomes with respect to expansion of antigen-specific T cells. In particular, bead:cell ratios can be varied to selectively expand or delete antigen-specific (memory) T cells. In one embodiment, the particular bead:cell ratio used selectively deletes antigen-specific T cells. In a further embodiment, the particular bead:cell ratio used selectively expands antigen-specific T cells. For example, bead to cell ratios of 1:100, 1:50, 1:25, 1:5 or 1:2.5 and the like are used to expand antigen-specific T cells. Low bead:cell ratio can help preserve and promote expansion of memory (antigen-specific) T cells. Additionally, when additional beads are added at very low ratios to cells (1:10, 1:25, 1:50, 1:100) at various days of culture (e.g. sequential addition at day 5, 7, or 9), one can enhance and even promote preferential expansion of the memory cells. With either 1:5 or 1:2.5 bead:cell ratio as initial stimulus, addition of 1:10, 1:25, and to some extent 1:50 and 1:100 bead:cell ratio at days 5 and 7 appear to preserve and enhance further expansion of memory cells that would otherwise not occur with a single stimulation at day 0 (see specifically Examples described herein). Therefore, the compositions and methods described herein can be used to expand specific populations of T cells, or to delete specific populations of T cells, for use in any variety of immunotherapeutic settings described herein.

It should be noted that the particle:cell ratios described herein can be used in any combination with the various ratios of antibodies bound on the beads. For example, beads containing about 1:5 to 1:10 ratio of anti-CD3/anti-CD28 antibodies bound thereto can be used at a ratio of about 1:5 to 1:10 particles:cell. Or, beads containing a 1:1 ratio of anti-CD3/anti-CD28 antibodies bound thereto can be used at a ratio of about 1:5 particles:cell, etc. Thus, the ratio of anti-CD3:anti-CD28 antibody bound to the beads ranges from 100:1 to 1:100 and all integer values there between and such beads can be used at a ratio of particle:cell of anywhere from about 1:500 to 500:1 and any integer values in between, in any combination.

Using certain methodologies it may be advantageous to maintain long-term stimulation of a population of T-cells following the initial activation and stimulation, by separating the T-cells from the stimulus after a period of about 12 to about 14 days. The rate of T-cell proliferation is monitored periodically (e.g., daily) by, for example, examining the size or measuring the volume of the T-cells, such as with a Coulter Counter. In this regard, a resting T-cell has a mean diameter of about 6.8 microns, and upon initial activation and stimulation, in the presence of the stimulating ligand, the T-cell mean diameter will increase to over 12 microns by day 4 and begin to decrease by about day 6. When the mean T-cell diameter decreases to approximately 8 microns, the T-cells may be reactivated and re-stimulated to induce further proliferation of the T-cells. Alternatively, the rate of T-cell proliferation and time for T-cell re-stimulation can be monitored by assaying for the presence of cell surface molecules, such as, CD 154, CD54, CD25, CD137, CD134, which are induced on activated T-cells.

In one embodiment, T-cell stimulation is performed with anti-CD3 and anti-CD28 antibodies co-immobilized on beads (3×28 beads), for a period of time sufficient for the cells to return to a quiescent state (low or no proliferation) (approximately 8-14 days after initial stimulation). The stimulation signal is then removed from the cells and the cells are washed and infused back into the patient. The cells at the end of the stimulation phase are rendered "super-inducible" by the methods of the present invention, as demonstrated by their ability to respond to antigens and the ability of these cells to demonstrate a memory-like phenotype, as is evidence by the examples. Accordingly, upon re-stimulation either exogenously or by an antigen in vivo after infusion, the activated T-cells demonstrate a robust response characterized by unique phenotypic properties, such as sustained CD154 expression and increased cytokine production.

In further embodiments of the present invention, the cells, such as T-cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, resulting in cell surface moiety ligation, thereby inducing cell stimulation.

In another embodiment, the time of exposure to stimulatory agents such as anti-CD3/anti-CD28 (i.e., CD3xCD28)-coated particles, such as beads, may be modified or tailored to obtain a desired T-cell phenotype. One may desire a greater population of helper T-cells ($T_H$), typically CD4$^+$ as opposed to CD8$^+$ cytotoxic or suppressor T-cells ($T_C$), because an expansion of $T_H$ cells could induce desired effector function (e.g., anti-tumor, anti-viral, anti-bacterial, and the like). CD4$^+$ T-cells, express important immune-regulatory molecules, such as GM-CSF, CD40L, and IL-2, for example. Where CD4-mediated help is preferred, a method, such as that described herein, which preserves or enhances the CD4:CD8 ratio could be of significant benefit. In one aspect of the present invention, it may be beneficial to increase the number of infused cells expressing GM-CSF, or IL-2, all of which are expressed predominantly by CD4$^+$ T-cells. Alternatively, in situations where CD4-help is needed less and increased numbers of CD8$^+$ T-cells are desirous, the T cell activation approaches described herein can also be utilized, by for example, pre-selecting for CD8$^+$ cells prior to stimulation and/or culture. Such situations may exist where increased levels of IFN-γ is preferred. Further, in other applications, it may be desirable to utilize a population of $T_H1$-type cells versus $T_H2$-type cells (or vice versa), or supernatants therefrom. Likewise, it may be desirable in certain applications to utilize a population of regulatory T cells (e.g., Autoimmun Rev. 2002 August; 1(4):190-7; Curr Opin Immunol. 2002 December; 14(6):771-8).

To effectuate isolation of different antigen-specific T-cell populations, times of cell surface moiety ligation that induces re-stimulation (activation) may be varied or pulsed. For example expansion times may be varied to obtain the specific phenotype of interest and/or different types of stimulatory agents may be used (e.g., antibodies or fragments thereof, a peptide, polypeptide, MHC/peptide tetramer, growth factor, cytokine, chemokine, glycopeptide, soluble receptor, steroid, hormone, mitogen, such as PHA, or other superantigens). The expression of a variety of phenotypic markers change over time; therefore, a particular time point or stimulatory agent may be chosen to obtain a specific population of T-cells. Accordingly, depending on the cell type to be stimulated, the stimulation and/or expansion time may be four weeks or less, 2 weeks or less, 10 days or less, or 8 days or less (four weeks or less includes all time ranges from 4 weeks down to 1 day (24 hours)). In some embodiments, stimulation and expansion may be carried out for 6 days or less, 4 days or less, 2 days or less, and in other embodiments for as little as 24 or less hours, and preferably 4-6 hours or less (these ranges include any integer values in between). When stimulation of T-cells is carried out for shorter periods of time, the population of T-cells may not increase in number as dramatically, but the population will provide robust and healthy activated antigen-specific T-cells that can continue to proliferate in vivo and more closely resemble the natural effector T-cell pool.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T-cells are cultured together for about eight days. In another embodiment, the beads and T-cells are cultured together for 2-3 days. Several cycles of stimulation may also be desired such that culture time of T cells can be 60 days or more. Conditions appropriate for T-cell culture include an appropriate media (e.g., Minimal Essential Media or RPMI Media 1640 or, X-vivo 15, (BioWhittaker)) that may contain factors necessary for proliferation and viability, including serum (e.g., fetal bovine or human serum), interleukin-2 (IL-2), insulin, IFN-γ, IL-4, GM-CSF, IL-10, IL-12, TGFβ, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, with added amino acids and vitamins, either serum-free or supplemented with an appropriate amount of serum (or plasma) or a defined set of hormones, and/or an amount of cytokine(s) sufficient for the growth and expansion of T-cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

In certain embodiments, it may be desirable to add some number of feeder cells to augment activation and/or expansion of antigen-specific cells. Feeder cells can encompass a variety of cell types, including, irradiated peripheral blood lymphocytes (autologous or allogeneic) alone or in combination with EBV-transformed B cell lines (autologous or allogeneic), immortalized or non-immortalized cell lines of the myelomonocytic lineage, such as macrophages, dentritic cells, red blood cells, B-cells, tumor cell lines such as U937, Jurkat, Daudi, MOLT-4, HUT, CEM, Colo 205, HTB-13, and HTB-70. Feeder cells need not be of human origin as long as they provide feeder function, e.g. the ability to facilitate the survival and growth of primary T cells and there derived antigen-specific clones.

Pharmaceutical Compositions

An additional aspect of the present invention provides a population or composition of antigen-specific T cells. The present invention further provides a pharmaceutical composition comprising antigen-specific T cells and a pharmaceutically acceptable carrier. Compositions of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as ethylenediaminetetraacetic acid (EDTA) or glutathione; adjuvants (e.g., aluminum hydroxide); and preservatives. Compositions of the present invention are, in certain aspects, formulated for intravenous administration.

A related embodiment of the present invention further provides a pharmaceutical composition comprising the antigen-specific T cells, and a pharmaceutically acceptable carrier. The pharmaceutically acceptable carrier should be sterilized by techniques known to those skilled in the art.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

The present invention also provides methods for preventing, inhibiting, or reducing the presence of a cancer or malignant cells in an animal, which comprise administering to an animal an anti-cancer effective amount of the subject antigen-specific T cells.

The cancers contemplated by the present invention, against which the immune response is induced, or which is to be prevented, inhibited, or reduced in presence, may include but are not limited to melanoma, non-Hodgkin's lymphoma, Hodgkin's disease, leukemia, plasmocytoma, sarcoma, glioma, thymoma, breast cancer, prostate cancer, colo-rectal cancer, kidney cancer, renal cell carcinoma, pancreatic cancer, esophageal cancer, brain cancer, lung cancer, ovarian cancer, cervical cancer, multiple myeloma, hepatoma, acute lymphoblastic leukemia (ALL), acute myelogenous leukemia (AML), chronic myelogenous leukemia (CML), chronic lymphocytic leukemia (CLL), low-grade lymphoma, and other neoplasms known in the art.

Alternatively, compositions as described herein can be used to induce or enhance responsiveness to pathogenic organisms, such as viruses, (e.g., single stranded RNA viruses, single stranded DNA viruses, human immunodeficiency virus (HIV), hepatitis A, B, and C virus, herpes simplex virus (HSV), cytomegalovirus (CMV) Epstein-Barr virus (EBV), Human Papilloma Virus (HPV)), parasites (e.g., protozoan and metazoan pathogens such as *Plasmodia* species, *Leishmania* species, *Schistosoma* species, *Trypanosoma* species), bacteria (e.g., *Mycobacteria, Salmonella,* Streptococci, *E. coli,* Staphylococci), fungi (e.g., *Candida* species, *Aspergillus* species) and *Pneumocystis carinii*.

In certain embodiments, the methods of the present invention can be used in conjunction with the generation of T regulatory cells for specific immunosuppression in the case of inflammatory disease, autoimmunity, and foreign graft acceptance. Regulatory T cells can be generated and expanded using the methods of the present invention. The regulatory T cells can be antigen-specific and/or polyclonal. Regulatory T cells can be generated using art-recognized techniques as described for example, in Woo, et al., J Immunol. 2002 May 1; 168(9):4272-6; Shevach, E. M., Annu. Rev. Immunol. 2000, 18:423; Stephens, et al., Eur. J. Immunol. 2001, 31:1247; Salomon, et al, Immunity 2000, 12:431; and Sakaguchi, et al., Immunol. Rev. 2001, 182:18. Accordingly, T cells of the present invention can be used for the treatment of autoimmune diseases such as, but not limited to, rheumatoid arthritis, multiple sclerosis, insulin dependent diabetes, Addison's disease, celiac disease, chronic fatigue syndrome, inflammatory bowel disease, ulcerative colitis, Crohn's disease, Fibromyalgia, systemic lupus erythematosus, psoriasis, Sjogren's syndrome, hyperthyroidism/Graves disease, hypothyroidism/Hashimoto's disease, Insulin-dependent diabetes (type 1), Myasthenia Gravis, endometriosis, scleroderma, pernicious anemia, Goodpasture syndrome, Wegener's disease, glomerulonephritis, aplastic anemia, paroxysmal nocturnal hemoglobinuria, myelodysplastic syndrome, idiopathic thrombocytopenic purpura, autoimmune hemolytic anemia, Evan's syndrome, Factor VIII inhibitor syndrome, systemic vasculitis, dermatomyositis, polymyositis and rheumatic fever.

The immune response induced in the animal by administering the subject compositions of the present invention may include cellular immune responses mediated by cytotoxic T cells, capable of killing tumor and infected cells, and helper T cell responses. Humoral immune responses, mediated primarily by helper T cells capable of activating B cells thus leading to antibody production, may also be induced. A variety of techniques may be used for analyzing the type of immune responses induced by the compositions of the present invention, which are well described in the art; e.g., Coligan et al. Current Protocols in Immunology, John Wiley & Sons Inc. (1994).

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient. It can generally be stated that a pharmaceutical composition comprising the subject antigen-specific T cells, may be administered at a dosage of $10^4$ to $10^7$ APC/kg body weight, preferably $10^5$ to $10^6$ APC/kg body weight, including all integer values within those ranges. Antigen-specific T cells compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

Typically, in adoptive immunotherapy studies, antigen-specific T cells are administered approximately at $2\times10^9$ to $2\times10^{11}$ cells to the patient. (See, e.g., U.S. Pat. No. 5,057, 423). In some aspects of the present invention, particularly in the use of allogeneic or xenogeneic cells, lower numbers of cells, in the range of $10^6$/kilogram ($10^6$-$10^{11}$ per patient) may be administered. In certain embodiments, T cells are administered at $1\times10^5$, $1\times10^6$, $1\times10^7$, $1\times10^8$, $2\times10^8$, $2\times10^9$, $1\times10^{10}$, $2\times10^{10}$, $1\times10^{11}$, $5\times10^{11}$, or $1\times10^{12}$ cells to the subject. T cell compositions may be administered multiple times at dosages within these ranges. The antigen-specific T cells may be autologous or heterologous to the patient undergoing therapy. If desired, the treatment may also include administration of mitogens (e.g., PHA) or lymphokines, cytokines, and/or chemokines (e.g., GM-CSF, IL-4, IL-13, Flt3-L, RANTES, MIP1α, etc.) as described herein to enhance induction of the immune response.

The administration of the subject pharmaceutical compositions may be carried out in any convenient manner, including by aerosol inhalation, injection, ingestion, transfusion, implantation or transplantation. The compositions of the present invention may be administered to a patient subcutaneously, intradermally, intramuscularly, by intravenous (i.v.) injection, or intraperitoneally. In one embodiment, the antigen-specific T cell compositions of the present invention are administered to a patient by intradermal or subcutaneous injection. In another embodiment, the antigen-specific T cell compositions of the present invention are preferably administered by i.v. injection. The compositions of antigen-specific T cells may be injected directly into a tumor or lymph node.

In yet another embodiment, the pharmaceutical composition can be delivered in a controlled release system. In one embodiment, a pump may be used (see Langer, 1990, Science 249:1527-1533; Sefton 1987, CRC Crit. Ref. Biomed. Eng. 14:201; Buchwald et al., 1980; Surgery 88:507; Saudek et al., 1989, N. Engl. J. Med. 321:574). In another embodiment, polymeric materials can be used (see Medical Applications of Controlled Release, 1974, Langer and Wise (eds.), CRC Pres., Boca Raton, Fla.; Controlled Drug Bioavailability, Drug Product Design and Performance, 1984, Smolen and Ball (eds.), Wiley, New York; Ranger and Peppas, 1983; J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, thus requiring only a fraction of the systemic dose (see, e.g., Medical Applications of Controlled Release, 1984, Langer and Wise (eds.), CRC Pres., Boca Raton, Fla., vol. 2, pp. 115-138).

The antigen-specific T cell compositions of the present invention may also be administered using any number of matrices. Matrices have been utilized for a number of years within the context of tissue engineering (see, e.g., Principles of Tissue Engineering (Lanza, Langer, and Chick (eds.)), 1997. The present invention utilizes such matrices within the novel context of acting as an artificial lymphoid organ to support, maintain, or modulate the immune system, typically through modulation of T cells. Accordingly, the present invention can utilize those matrix compositions and formulations which have demonstrated utility in tissue engineering. Accordingly, the type of matrix that may be used in the compositions, devices and methods of the invention is virtually limitless and may include both biological and synthetic matrices. In one particular example, the compositions and devices set forth by U.S. Pat. Nos. 5,980,889; 5,913,998; 5,902,745; 5,843,069; 5,787,900; or 5,626,561 are utilized. Matrices comprise features commonly associated with being biocompatible when administered to a mammalian host. Matrices may be formed from both natural or synthetic materials. The matrices may be non-biodegradable in instances where it is desirable to leave permanent structures or removable structures in the body of an animal, such as an implant; or biodegradable. The matrices may take the form of sponges, implants, tubes, telfa pads, fibers, hollow fibers, lyophilized components, gels, powders, porous compositions, or nanoparticles. In addition, matrices can be designed to allow for sustained release seeded cells or produced cytokine or other active agent. In certain embodiments, the matrix of the present invention is flexible and elastic, and may be described as a semisolid scaffold that is permeable to substances such as inorganic salts, aqueous fluids and dissolved gaseous agents including oxygen.

A matrix is used herein as an example of a biocompatible substance. However, the current invention is not limited to matrices and thus, wherever the term matrix or matrices appears these terms should be read to include devices and other substances which allow for cellular retention or cellular traversal, are biocompatible, and are capable of allowing traversal of macromolecules either directly through the substance such that the substance itself is a semi-permeable membrane or used in conjunction with a particular semi-permeable substance.

In certain embodiments of the present invention, the cells of the present invention are administered to a patient in conjunction with (e.g. before, simultaneously or following) any number of relevant treatment modalities, including but not limited to treatment with agents such as antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxin, fludaribine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993; Isoniemi (supra)). In a further embodiment, the cell compositions of the present invention are administered to a patient in conjunction with (e.g. before, simultaneously or following) T-cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g. Rituxan. The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766.

All references referred to within the text are hereby incorporated by reference in their entirety. Moreover, all numerical ranges utilized herein explicitly include all integer values within the range and selection of specific numerical values within the range is contemplated depending on the particular use. Further, the following examples are offered by way of illustration, and not by way of limitation.

EXAMPLES

Example 1

CMV Antigen Coated Beads Activate and Facilitate Isolation of Antigen-Specific T Cells In this experiment, cytomegalovirus (CMV)-coated beads were used to activate and isolate antigen-specific T cells.

CMV lysate prepared using standard techniques was mixed at room temperature for 1-2 hours with Dynabead M-450 while rotating. Beads were then washed once, and added to PBMC. Within hours, the beads were phagocytosed in the APC. Within 72 hours, CMVpp65-HLA-A2 tetramers detected CD25-high (activated) T cell specific for CMV pp65. Magnetic selection of the bead-loaded APC with the associated antigen-specific T cells was carried out at day 5, thereby enriching for CMV-specific T cells. As shown in FIG. 1, following magnetic separation, CMV-specific T cells were still tightly associated with bead-loaded APC. It should be noted that magnetic separation can be carried out anywhere from about day 1 to about day 10.

Example 2

Memory CD8 CMV Tetramer+ T Cells Expanded Ex Vivo Up-Regulate CD25 Upon Re-Stimulation In this example, antigen-coated beads were used to activate CMV-specific CD8+ T cells ex vivo.

Figure 2:
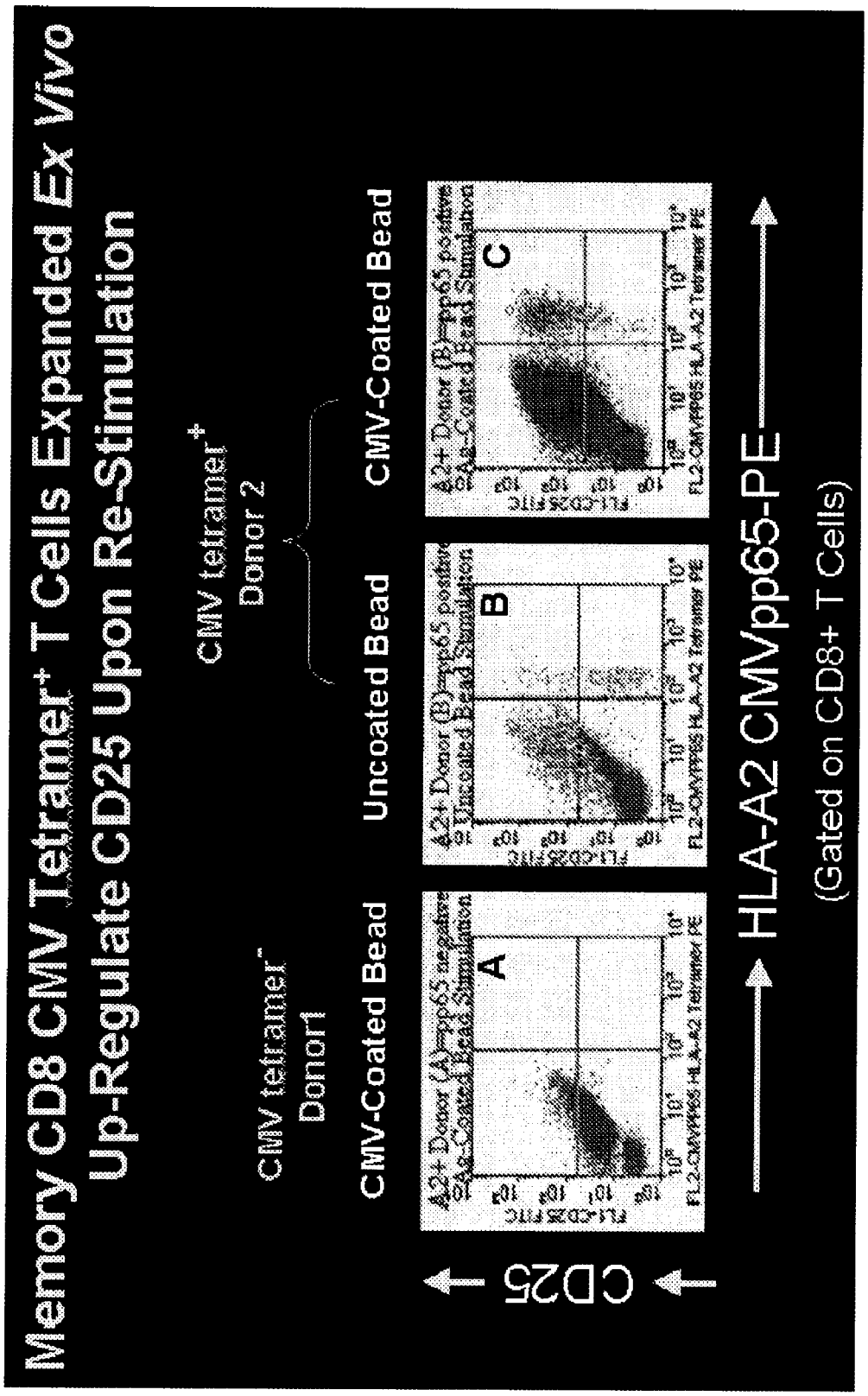
FIG. 2 is a plot showing upregulation of CD25 in re-stimulated memory CD8 CMV tetramer+ T cells expanded ex vivo. Panel A is a negative control from an HLA-A2+, CMV– donor. Panel B is a negative control showing uncoated bead stimulation from an HLA-A2+, CMV+ donor. Panel C shows CMV antigen-coated bead stimulation of cells from an HLA-A2+, CMV+ donor.

PBMC from CMV pp65 tetramer-positive and tetramer-negative donors were stimulated with paramagnetic Dynal M-450 beads coated with CMV lysate. As controls, CMV pp65 tetramer-negative PBMC were cultured with CMV-lysate coated beads (FIG. 2, panel A), CMV pp65 tetramer-positive PBMC were cultured with "naked" beads (no CMV antigen) (FIG. 2, panel B). CMV pp65 tetramer-positive PBMC were cultured with CMV-lysate coated beads (FIG. 2, panel C). Following stimulation, activation of CMV-specific T cells was measured on Day 10 by CMV pp65 HLA-A2 tetramer stain and CD25 expression as an indicator of activation. As shown in FIG. 2, up-regulation of CD25 was observed in memory CD8 CMV tetramer+ T cells expanded ex vivo using antigen-coated beads.

Antigen-coated beads can be used to activate and stimulate antigen-specific T cells. These antigen-specific T cells can then be enriched as described in Example 1 and elsewhere herein. These antigen-specific T cells can be further expanded as described herein and in U.S. patent application Ser. Nos. 10/350,305, 10/187,467, 10/133,236, 09/960,264, and 09/794,230. The antigen-specific T cells of the present invention can be used in any number of immunotherapeutic settings as described herein.

Example 3

Varying Bead:Cell Ratios can Selectively Expand or Delete Memory CD8 T Cells

This example shows that the bead:cell ratio can have a profound effect on expansion of different populations of T cells. In particular, a high bead:cell ratio (3:1-10:1, 20:1 and higher) tends to induce death in antigen-specific T cells while a lower bead:cell ratio (1:1-1:10, 1:20, 1:30, 1:40, 1:50 or lower) leads to expansion of antigen-specific T cells. Further, the data described below show that lower bead:cell ratios lead to improved cell expansion in polyclonal cell populations as well. Thus, this example shows that lower bead:cell ratios improve overall cell expansion.

Cells were prepared and stimulated using the XCELLERATE I™ process essentially as described in U.S. patent application Ser. No. 10/187,467 filed Jun. 28, 2002. Briefly, in this process, the XCELLERATED™ T-cells are manufactured from a peripheral blood mononuclear cell (PBMC) apheresis product. After collection from the patient at the clinical site, the PBMC apheresis are washed and then incubated with "uncoated" DYNABEADS® M-450 Epoxy T. During this time phagocytic cells such as monocytes ingest the beads. After the incubation, the cells and beads are processed over a MaxSep Magnetic Separator in order to remove the beads and any monocytic/phagocytic cells that are attached to the beads. Following this monocyte-depletion step, a volume containing a total of $5 \times 10^8$ CD3+ T-cells is taken and set-up with $1.5 \times 10^9$ DYNABEADS® M-450 CD3/CD28 T to initiate the XCELLERATE™ process (approx. 3:1 beads to T-cells). The mixture of cells and DYNABEADS® M-450 CD3/CD28 T are then incubated at 37° C., 5% $CO_2$ for approximately 8 days to generate XCELLERATED T-cells for a first infusion. The remaining monocyte-depleted PBMC are cryopreserved until a second or further cell product expansion (approximately 21 days later) at which time they are thawed, washed and then a volume containing a total of $5 \times 10^8$ CD3+ T-cells is taken and set-up with $1.5 \times 10^9$ DYNABEADS® M-450 CD3/CD28 T to initiate the XCELLERATE Process for a second infusion. During the incubation period of 8 days at 37° C., 5% $CO_2$, the CD3+ T-cells activate and expand. The anti-CD3 mAb used is BC3 (XR-CD3; Fred Hutchinson Cancer Research Center, Seattle, Wash.), and the anti-CD28 mAb (B-T3, XR-CD28) is obtained from Diaclone, Besançon, France.

For the experiment described below, prior to plating and culturing, the monocyte depleted cells were mixed by rotation for 30 minutes with varying amounts of beads as summarized below in Table 1. The beads used in this Example comprised the DYNABEADS® M-450 CD3/CD28 T with a 1:1 CD3:CD28 antibody ratio bound on the beads.

TABLE 1

Varying Bead:Cell Ratios can Selectively Expand or Delete Memory CD8 T cells

| Bead:Cell Ratio | Fold Increase | |
|---|---|---|
| | Polyclonal T cells | CMV Antigen-Specific T cells |
| 10:1 | 149 | 0 |
| 5:1 | 294 | 0 |
| 3:1 | 346 | 1.4 |
| 1:1 | 562 | 20.6 |
| 1:5 | 113 | 53 |
| 1:10 | 79 | 45.8 |

Figure 3:
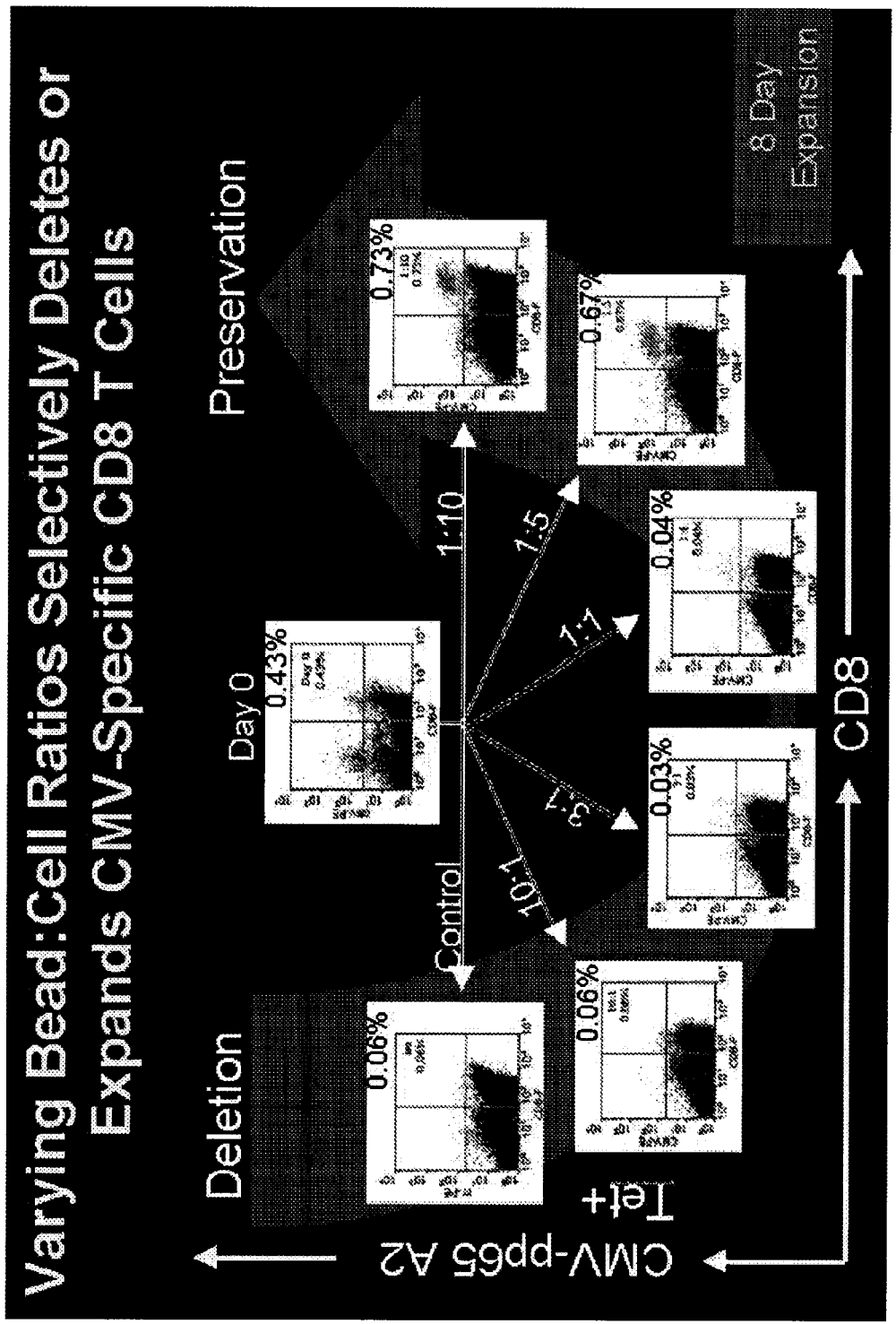
FIG. 3 is a plot showing the effect of varying bead:cell ratio on expansion or deletion of CMV-specific T cells.

The results summarized in Table 1 and shown graphically in FIG. 3 demonstrate that antigen-specific T cells can be selectively deleted by using high bead:cell ratios and expanded using low bead:cell ratios (similar results were observed with Influenza- and EBV-specific cells). Without being bound by theory, it is thought that the antigen-specific T cells are sensitized to further stimulation. Thus, the key appears to be the strength of the T cell activation signal: selective expansion of memory T cells (antigen-specific T cells) occurs with "weak" signals while selective deletion of memory T cells occurs with "strong" signals. The quantity of the CD3/TCR (and CD28) receptors that bound by ligands determines the signal strength. Thus, stimulation with high bead:cell ratios provides a high concentration of stimulating antibody (i.e., "strong signal"), leading to over-stimulation of antigen-specific T cells, causing them to die, either by apoptosis or other mechanisms. Using lower bead:cell ratios provides a stimulation signal to antigen-specific T cells that does not over-stimulate, but rather induces rapid proliferation of these cells.

In further experiments, fold increase of antigen-specific (e.g., CMV tetramer positive cells) was shown to be excellent using a 1:30 ratio and also using beads bound with anti-4-1BB antibody.

Therefore, in this Example, evidence is provided to support the use of differing bead:cell ratios depending on the outcome desired. For expansion of antigen-specific T cells, a lower bead:cell ratio is preferable.

Example 4

Varying Bead:Cell Ratios and Sequential Addition of Beads During Culture Can Improve Expansion of Memory T Cells This example shows that sequential addition of beads at a low bead:cell ratio during culture can improve expansion of memory T cells.

Figure 4:
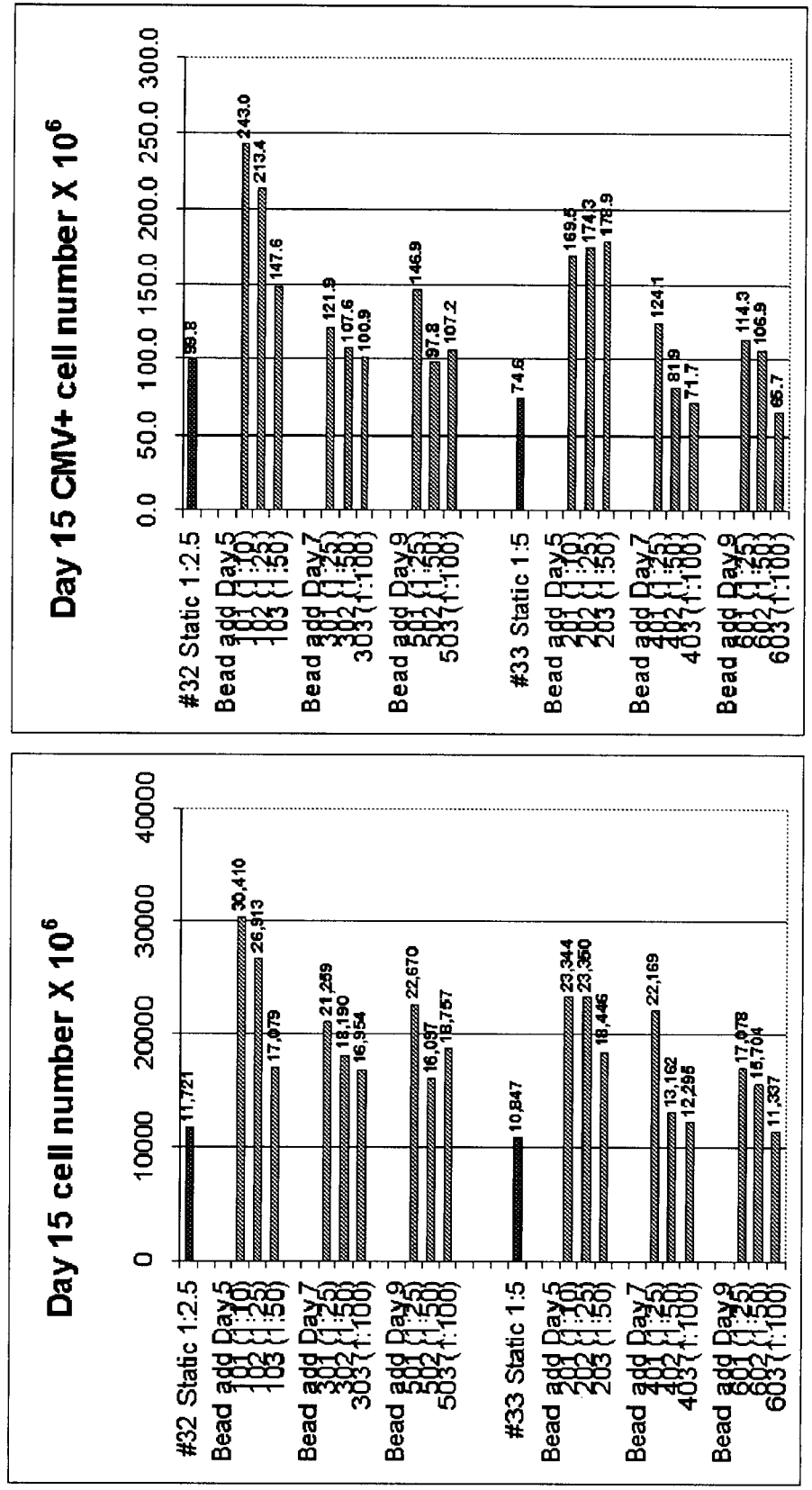
FIG. 4 panels A and B is a bar graph showing the effect on T cell expansion of sequential bead addition at varying bead: cell ratios at varying times during culture. Panel A shows a comparison of total T cell expansion over 15 days, comparing standard static culture (beads at day 0 at either 1:2.5 or 1:5 bead to cell ratio) or additional beads added at day 5, 7, or 9 at 1:10, 1:25, 1:50 or 1:100 bead to cell ratios. Panel B shows CMV-specific T cell expansion under the same experimental conditions as Panel A.

Cells were prepared and stimulated essentially as described in Example 3 with the following modifications: as shown in FIG. 4, panels A and B, cells were cultured either at a starting static culture with a bead:cell ratio of 1:2.5 or 1:5 OR at 1:2.5 or 1:5 starting ratio with additional beads added at day 5, 7, or 9 at 1:10, 1:25, 1:50 or 1:100 ratios as noted. A comparison of total T cell expansion over 15 days shows an increase in expansion of cells when beads are added sequentially over culturing time, in cultures with both starting bead:cell ratios of 1:2.5 and 1:5. Comparison of CMV-specific T cell expansion over 15 days also shows an increase in expansion of antigen-specific cells when beads are added sequentially during culture (see FIG. 4 panel A and FIG. 4 panel B). The most dramatic increase in expansion of polyclonal cells and antigen-specific T cells over static culture was observed in those cultures where beads were added at day 0 at a ratio of 1:2.5 beads:cells and sequentially added at a 1:10 ratio at day 5.

Figure 5:
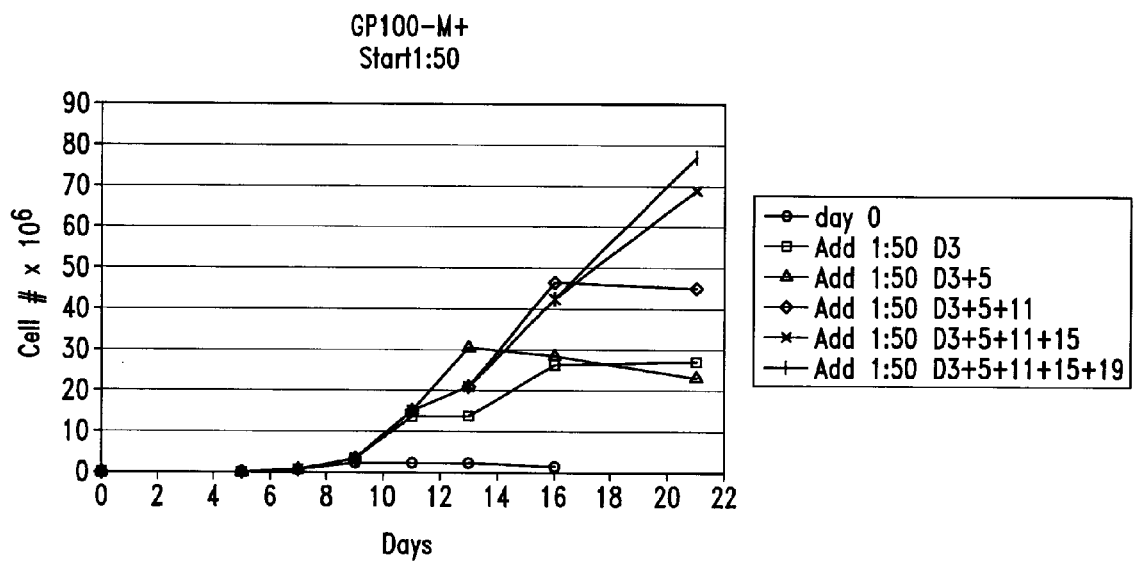
FIG. 5 is a graph showing the effect on T cell expansion of low bead:T cell ratio and sequential addition of beads on Melanoma gp100(M)-specific T cells.

In a related experiment, reduced bead:cell ratio and sequential addition was used to examine expansion of T cells from patients vaccinated with Melanoma gp100(M). As shown in FIG. 5, using a reduced bead:T cell ratio of 1:50 and sequential addition at days 3, 5, 11, 15, and 19, a dramatic increase in expansion was observed in Melanoma gp100(M)-specific T cells.

Example 5

Assessment of $CD4^+$ T Memory ("Antigen-Experienced") T Cells in the Xcellerate Expansion Process This example describes a model system for assessing CD4 T cell subsets in the Xcellerate expansion process.

Toxic Shock Syndrome Toxin (TSST) is a superantigen that specifically stimulates CD4+ T cells expressing TCR Vβ2. PBMC are composed of between 1-25% Vβ2 TCR T cells. A $CD4^+$ Vβ2 specific cell line is generated by stimulating PBMC with TSST for 9-14 days until T cells proliferate out of log phase. These "antigen experienced" Vβ2 T cells are then mixed back at varying percentages of the total culture (e.g., 1%, 2%) with a Vβ2 depleted naïve PBMC culture and stimulated with CD3/CD28 beads at varying bead:cell ratios as described herein in the Xcellerate™ process.

The results showed that the presence of TSST expanded CD4+ Vβ2 TCR T cells does not inhibit total T cell Xcellerate™ expansion, with total T cell fold increases in the normal range. Further, confirming other experiments, antigen-specificity was maintained during expansion and antigen experienced Vβ2 TCR T cells expanded well at bead:cell ratios of 1:10 and 1:30.

Example 6

T Cell Expansion Using Varying Anti-CD3:Anti-CD28 Antibody Ratios

Figure 6:
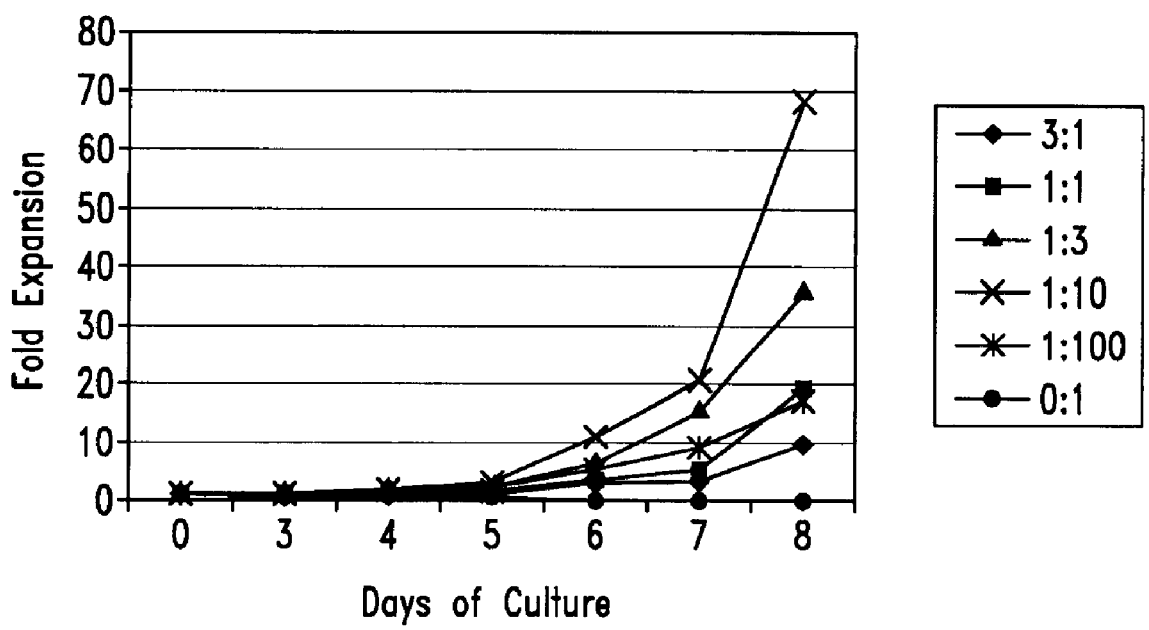
FIG. 6 is a graph depicting the fold increase of T-cells over time following stimulation with anti-CD3 and anti-CD28 co-immobilized beads with varying ratios of anti-CD3:CD28 antibodies attached thereto.
Figure 7:
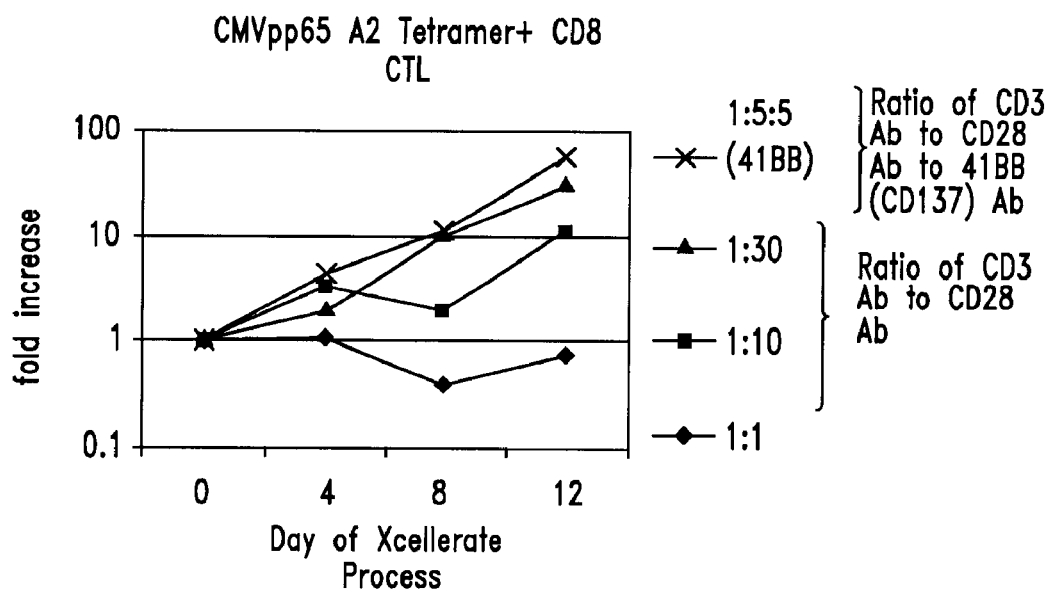
FIG. 7 is a graph depicting the fold increase of CMVpp65-specific T-cells over time following stimulation with anti-CD3 and anti-CD28 co-immobilized beads with varying ratios of anti-CD3:CD28 antibodies attached thereto.

T cell expansion was evaluated using varying concentrations of anti-CD3:anti-CD28 antibody ratios on the 3×28 DYNABEADS® M-450. In the experiments described herein, the process referred to as XCELLERATE II™ was used, as described in U.S. patent application Ser. No. 10/187,467. Briefly, this process is similar to XCELLERATE 1™ as described in Example 3 with some modifications in which no separate monocyte depletion step was utilized and in certain processes the cells were frozen prior to initial contact with beads and further concentration and stimulation were performed. As shown in FIG. 6, surprisingly, about a 68-fold expansion after 8 days of culture was observed with an anti-CD3:CD28 ratio of 1:10 antibodies on the beads. A 35-fold expansion of T cells was seen after 8 days of culture with a CD3:CD28 ratio of 1:3 on the beads. At a 1:1 ratio, about a 24-fold expansion was seen. As shown in FIG. 7, similar results were observed with CMVpp65-specific $CD8^+$ T cells using anti-CD3:anti-CD28 antibody ratios as low as 1:30.

Example 7

T Cell Expansion Using the Xcellerate Process and the Wave Bioreactor

This example describes the T cells expansion using essentially the XCELLERATE™ II process as described in U.S.

patent application Ser. Nos. 10/350,305; 10/187,467; 10/133, 236; 09/960,264; 09/794,230; PCT/US01/06139; and PCT/US02/28161, followed by seeding cells into the WAVE BIOREACTOR®.

Day 0 of the Xcellerate Process—On the first day of the XCELLERATE™ process essentially, the required number of cryopreserved Cryocte™ containers from were removed from the storage freezer, thawed washed and filtered.

Day 0—A volume of cells containing approximately $0.5 \times 10^9$ CD3$^+$ cells was then mixed with DYNABEADS® M-450 CD3/CD28 T at a ratio of 3:1 DYNABEADS® M-450 CD3/CD28 T:CD3$^+$ T cells and incubated with rotation. After the incubation, the CD3$^+$ T cells were magnetically concentrated and simultaneously activated. The CD3$^+$ T cells were then resuspended in complete medium in a Lifecell Cell Culture Bag. The bag containing the cells and beads was then placed in a patient-dedicated incubator (37° C., 5% $CO_2$).

On or around Day 3—The CD3$^+$ cells were culture-expanded for 3 days at which point the contents of the single bag are split into 4 new Lifecell bags. The 4 bags were then returned to the patient-dedicated incubator (37° C., 5% $CO_2$).

On or around Day 5—The CD3' cells were culture-expanded for ≈2 additional days at which point the contents of the culture bags were then seeded into a 20 L WAVE BIOREACTOR® containing a 10 L volume of media. The cells were then cultured at 37° C., 5% $CO_2$ with the wave motion at 15 rocks/minute and with perfusion at 1 ml/minute.

Cell counts were determined each day and compared to cells stimulated and expanded using the static XCELLERATE™ II process. Expansion was dramatically improved when cells were cultured in The WAVE BIOREACTOR®. Further, cell densities reached as high as $50 \times 10^6$ cells/ml in The Wave Bioreactor, as compared to a maximum cell density of $5 \times 10^6$ observed in the static XCELLERATE™ II process. A total cell count of about 800 billion was achieved at day 12 of culture from a starting cell count of about $0.5 \times 10^9$ cells using The WAVE BIOREACTOR®.

Thus, The WAVE BIOREACTOR® provides an unexpected and dramatic improvement to the expansion process. Furthermore, hitherto unobserved cell densities and final absolute cell yields were achieved using The WAVE BIOREACTOR®.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for generating and/or enriching antigen-specific T cells comprising:
   (a) exposing a first population of cells wherein at least a portion thereof comprises antigen presenting cells to a paramagnetic bead wherein said paramagnetic bead has antigen attached thereto, such that said paramagnetic bead with antigen attached thereto is ingested by said APC;
   (b) exposing a second population of cells wherein at least a portion thereof comprises T cells to the population of cells in part (a); thereby generating and/or enriching antigen-specific T cells through direct contact between said APC and said T cells; and
   (c) isolating said APCs and antigen-specific T cells by means of a magnetic field.

2. The method according to claim 1 wherein said antigen-specific T cells are expanded according to the following method:
   (a) exposing said T cells to an anti-CD3 antibody which is immobilized on a surface; and
   (b) stimulating an accessory molecule on the surface of the T cells with an anti-CD28 antibody, wherein said anti-CD28 antibody is immobilized on the same surface as the anti-CD3 antibody;
   thereby inducing expansion of said antigen-specific T cells.

3. The method according to claim 2, further comprising exposing said T cells to IL-15.

4. The method according to claim 2, further comprising exposing said T cells to a natural ligand for CD137.

5. The method according to claim 2, further comprising exposing said T cells to an anti-CD137 antibody.

6. The method according to claim 2, further comprising exposing said T cells to an anti-NKG2D antibody or a natural ligand for NKG2D.

7. The method according to claim 2 wherein said antigen-specific T cells are expanded by exposing said antigen-specific T cells to a mitogen.

8. The method according to claim 7 wherein said mitogen is selected from the group consisting of phytohemagglutinin (PHA), phorbol myristate acetate (PMA) and ionomycin, lipopolysaccharide (LPS), and superantigen.

9. The method according to claim 1 wherein said antigen is selected from the group consisting of protein, glycoprotein, peptides, antibody/antigen complexes, whole tumor or virus-infected cells, fixed tumor or virus-infected cells, heat-killed tumor or virus-infected cells, tumor lysate, non-soluble cell debris, apoptotic bodies, necrotic cells, whole tumor cells from a tumor or a cell line that have been treated such that they are unable to continue dividing, allogeneic cells that have been treated such that they are unable to continue dividing, irradiated tumor cells, irradiated allogeneic cells, natural or synthetic complex carbohydrates, lipoproteins, lipopolysaccharides, transformed cells or cell line, transfected cells or cell line, transduced cells or cell line, and virally infected cells or cell line.

10. The method according to claim 1 wherein said antigen is attached to said surface by an antibody/ligand interaction.

11. The method according to claim 10 wherein said antibody/ligand interaction comprises an interaction between an antibody/ligand pair selected from the group consisting of anti-MART-1 antibody/MART-1 antigen, anti-WT-1 antibody/WT-1, anti-PR1 antibody/PR1, anti-PR3 antibody/PR3, anti-tyrosinase antibody/tyrosinase antigen, anti-MAGE-1 antibody/MAGE-1 antigen, anti-MUC-1 antibody/MUC-1 antigen, anti-α-fetoprotein antibody/α-fetoprotein antigen, anti-Her2Neu antibody/Her2Neu, anti-HIV gp120 antibody/HIV gp120, anti-influenza HA antibody/influenza HA, anti-CMV pp65/CMV pp65, anti-hepatitis C antibody/hepatitis C proteins, anti-EBV EBNA 3B antibody/EBV EBNA 3B antigen, and anti-human Ig heavy and light chains/Ig from a myeloma cancer patient, and anti-human Ig heavy and light chains/Ig from a CLL cancer patient.

12. The method according to claim 1 wherein said antigen is chemically attached to said surface.

13. The method according to claim 1 wherein the attachment of said antigen to said surface comprises a biotin-avidin interaction.

14. The method according to claim 1 wherein said population of cells wherein at least a portion thereof comprises APC is derived from a source selected from the group consisting of leukapheresis product, peripheral blood, lymph node, tonsil, thymus, tissue biopsy, tumor, spleen, bone marrow, cord blood, CD34 cells, monocytes, and adherent cells.

* * * * *